(12) United States Patent
Grewe

(10) Patent No.: US 9,044,305 B2
(45) Date of Patent: Jun. 2, 2015

(54) SELF CLEANING DEVICES, SYSTEMS AND METHODS OF USE

(75) Inventor: David D. Grewe, West Lafayette, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 1816 days.

(21) Appl. No.: 12/416,486

(22) Filed: Apr. 1, 2009

(65) Prior Publication Data

US 2009/0254172 A1 Oct. 8, 2009

Related U.S. Application Data

(60) Provisional application No. 61/042,083, filed on Apr. 3, 2008.

(51) Int. Cl.
| | |
|---|---|
| *A61M 29/00* | (2006.01) |
| *A61F 2/01* | (2006.01) |
| *A61F 2/856* | (2013.01) |
| *A61F 2/86* | (2013.01) |
| *A61F 2/00* | (2006.01) |

(52) U.S. Cl.
CPC ............... *A61F 2/01* (2013.01); *A61F 2/0077* (2013.01); *A61F 2/856* (2013.01); *A61F 2/86* (2013.01); *A61F 2250/0039* (2013.01); *A61F 2002/018* (2013.01); *A61F 2230/0006* (2013.01); *A61F 2230/0008* (2013.01); *A61F 2230/0067* (2013.01); *A61F 2230/0069* (2013.01); *A61F 2230/008* (2013.01); *A61F 2220/0008* (2013.01); *A61F 2220/0016* (2013.01); *A61F 2220/005* (2013.01); *A61F 2220/0058* (2013.01); *A61F 2220/0075* (2013.01); *A61F 2230/0071* (2013.01)

(58) Field of Classification Search
USPC ............... 606/200; 623/1.11, 1.12, 1.15, 1.16
See application file for complete search history.

(56) References Cited

U.S. PATENT DOCUMENTS

| | | | |
|---|---|---|---|
| 4,739,762 | A | 4/1988 | Palmaz |
| 5,133,732 | A | 7/1992 | Wiktor |
| 5,292,331 | A | 3/1994 | Boneau |

(Continued)

FOREIGN PATENT DOCUMENTS

| | | |
|---|---|---|
| WO | WO 99/65417 | 12/1999 |
| WO | WO 00/53119 | 9/2000 |

(Continued)

OTHER PUBLICATIONS

International Search Report mailed Jul. 16, 2009 for PCT/US2009/002020, filed Apr. 1, 2009.

(Continued)

*Primary Examiner* — Dianne Dornbusch
*Assistant Examiner* — Michael Mendoza
(74) *Attorney, Agent, or Firm* — Brinks Gilson & Lione

(57) ABSTRACT

The invention relates to medical devices, systems and methods for preventing the embolic material flowing about a junction of at least one branch blood vessel and another blood vessel from entering the other blood vessel. The device includes a self cleaning flexible filter and a frame. The external surface of the filter is configured to temporarily trap at least some of the embolic material flowing about the junction as a result of the blood inflow though the filter. The filter is also configured to expel the trapped embolic material into the other blood vessel.

20 Claims, 23 Drawing Sheets

(56) References Cited

U.S. PATENT DOCUMENTS

| | | | |
|---|---|---|---|
| 5,421,955 | A | 6/1995 | Lau et al. |
| 6,090,127 | A | 7/2000 | Globerman |
| 6,692,513 | B2 * | 2/2004 | Streeter et al. ............... 606/200 |
| 7,232,453 | B2 | 6/2007 | Shimon |
| 7,306,575 | B2 | 12/2007 | Barbut et al. |
| 7,318,998 | B2 | 1/2008 | Goldstein et al. |
| 2003/0187495 | A1 * | 10/2003 | Cully et al. ............... 623/1.15 |
| 2004/0167613 | A1 * | 8/2004 | Yodfat et al. ............... 623/1.15 |
| 2004/0215167 | A1 | 10/2004 | Belson et al. |
| 2004/0220611 | A1 | 11/2004 | Ogle |
| 2004/0236407 | A1 | 11/2004 | Fierens et al. |
| 2005/0267516 | A1 | 12/2005 | Soleimani et al. |
| 2006/0015138 | A1 * | 1/2006 | Gertner ..................... 606/200 |
| 2006/0161241 | A1 | 7/2006 | Barbut et al. |
| 2007/0060994 | A1 | 3/2007 | Gobran et al. |
| 2007/0270901 | A1 | 11/2007 | Shimon et al. |
| 2008/0065145 | A1 | 3/2008 | Carpenter |

FOREIGN PATENT DOCUMENTS

| | | |
|---|---|---|
| WO | WO 02/055125 | 7/2002 |
| WO | WO 2006/076505 | 7/2006 |
| WO | WO 2006/105856 | 10/2006 |

OTHER PUBLICATIONS

Bayard et al., "Transcatheter Occlusion of the Left Atrial Appendage for Stroke Prevention," *Expert Rev of Cardiovascular Therapy*, 3(6):1003-1008 (2005).

Eifert et al., "Neurological and Neuropsychological Examination and Outcome After use of an Intra-Aortic Filter Device During Cardiac Surgery," *Perfusion*, 18:55-60 (2003).

Kipshidze et al., "Advanced c-myc Antisense (AVI-4126)-Eluting Phosphorylcholine-Coated Stent Implantation is Associated with Complete Vascular Healing and Reduced Neointimal Formation in the Porcine Coronary Restenosis Model," *Catheter Cardiovac Interv.*, 61(4):518-527 (2004).

Marshall et al., "Carotid Flow Rates and Flow Division at the Bifurcation in Healthy Volunteers," *Physiol. Meas.*, 25:691-697 (2004).

Nakai et al., "Percutaneous Left Atrial Appendage Occlusion (PLAATO) for Preventing Cardioembolism: First Experience in Canine Model," *Circulation*, 105:2217-2222 (2002).

Remington's Pharmaceutical Sciences, Chapter 43, 14th Ed., Mack Publishing Co., Easton, PA. (1986).

Rodenberg and Pavalco, "Peptides Derived from Fibronectin Type III Connecting Segments Promote Endothelial Cell Adhesion but Not platelet Adhesion: Implications in Tissue-Engineered Vascular Grafts," *Tissue Engineering*, 13(11):2653-2666 (2007).

* cited by examiner

SELF CLEANING DEVICES, SYSTEMS AND METHODS OF USE

RELATED APPLICATIONS

The present patent document claims the benefit of the filing date under 35 U.S.C. §119(e) of Provisional U.S. Patent Application Ser. No. 61/042,083, filed Apr. 3, 2008, which is hereby incorporated by reference.

BACKGROUND

1. Technical Field

The present invention relates to medical devices, systems and methods. More particularly, the present invention relates to devices, systems and methods for preventing the embolic material from entering carotid arteries that supply blood to the brain.

2. Background Information

Cerebrovascular diseases are considered among the leading causes of mortality and morbidity in the modern age. Strokes denote an abrupt impairment of brain function caused by pathologic changes occurring in blood vessels. The main cause of strokes is insufficient blood flow to the brain (i.e., ischemic stroke), which accounts for about 80% of stroke cases.

Ischemic strokes are generally caused by a sudden occlusion of an artery supplying the blood to the brain. Total occlusions or partial occlusions (i.e., stenosis) are often the result of diseases of the arterial wall. Arterial atherosclerosis is by far the most common arterial disorder, and when complicated by thrombosis or embolism it often is the most frequent cause of cerebral ischemia and infarction, resulting in cerebral stroke.

Cardioembolism causes about 15-20% of all strokes. Stroke caused by heart disease is primarily due to embolism of thrombotic material forming on the atrial or ventricular wall or the left heart valves. These thrombi can then detach and embolize into the arterial circulation. Emboli large enough can occlude large arteries in the brain territory and cause strokes.

Cardiogenic cerebral embolism is presumed to have occurred when cardiac arrhythmia or structural abnormalities are found or known to be present. The most common causes of cardioembolic stroke are nonrheumatic (non-valvular) atrial fibrillation (AF), prosthetic valves, rheumatic heart disease (RHD), ischemic cardiomyopathy, congestive heart failure, myocardial infarction, post-operatory state and protruding aortic arch atheroma (A.A.A.).

Such disorders may be treated in various ways. For example, the disorders may be treated by drug management, surgery (carotid endarterectomy) in case of occlusive disease, and or carotid angioplasty and carotid stents.

While endarterectomy, angioplasty and carotid stenting are procedures targeted at opening the occluded artery, they do not prevent progression of new plaque. Even more so, the above treatment methods only provide a solution to localized problems and do not prevent proximal embolic sources, i.e., embolus formed at remote sites (heart and ascending aorta) to pass through the reopened stenosis in the carotid and occlude smaller arteries in the brain. This is a substantial problem, inasmuch as about one-third of patients suffering from carotid occlusion also have proximal embolic sources leading to stroke. It should be noted that only about 20% of the cases of stroke result from an occlusion of the carotid arteries.

It will also be appreciated that endarterectomy is not suitable for intracranial arteries or in the vertebrobasilar system since these arteries are positioned within unacceptable environment (brain tissue, bone tissue) or are too small in diameter.

Introducing filtering means into blood vessels, in particular into veins, has been known for some time. However, filtering devices known in the art are generally of a complex design, which renders such devices unsuitable for implantation within branchiocephalic and or carotid arteries, and unsuitable for handling fine embolic material. Also, the filtering devices known in the art often become clogged and need to be cleaned or replaced. However, when considering the possible cerebral effects of even fine embolic material occluding an artery supplying blood to the brain, the consequences may be fatal or may cause irreversible brain damage.

In light of the short period of time during which brain tissue can survive without blood supply, there is significant importance to constantly providing suitable means for preventing even small embolic material from entering the carotid arteries, so as to avoid stroke and brain damage.

U.S. Pub. No. 2004/0167613 describes implantable devices for positioning about a blood vessel bifurcation zone to control flow of embolic material around the bifurcation. This device includes an anchoring element extending within the zone of bifurcation to anchor the device therein, and a deflecting element, associated with the anchoring element. The deflecting element includes a mesh having a mesh size sufficient to allow passage of blood without hindrance whilst preventing the passage of embolic material exceeding a predetermined size.

U.S. Pub. No. 2006/0161241 A1 discuses methods for treating mobile aortic atheroma, the method includes providing a radially expanding stent-like device and deploying distal protection device(s), such as a filter.

The left atrial appendage (LAA) is one of the most frequent sources of cardiogenic thrombi in patients with atrial fibrillation. There are two devices that are used for closing LAA from circulation and to prevent cardioembolic events: the Percutaneous Left Atrial Appendage Transcatheter Occlusion (PLAATO™) system (ev3 Inc., Plymouth, Minn., USA) and the WATCHMAN® filter system (Atritech Inc., Plymouth, Minn., USA).

Nakai et al. (Nakai et al., *Circulation*, 105:2217-2222 (2004) describe the PLAATO™ device, which is a LAA occlusion system that consists of an implant and a delivery catheter. The implant is composed of a nitinol metal cage with multiple struts that are outwardly bent. The device includes an occlusive membrane of expanded polytetrafluoroethylene (ePTFE), which is laminated directly to the frame, and is supported so that the perimeter has intimate contact with the inner wall of the appendage.

Bayard Y et al. (Bayard Y et al., *Expert Rev of Cardiovascular Therapy*, 3(6):1003-1008 (2005)) describe the PLAATO™ and the WATCHMAN® devices. The WATCHMAN® filter system consists of a nitinol framework and it is covered with a thin permeable polyester membrane with pores.

U.S. Pat. Pub. 2007/0060994 describes a blood flow diverter device for treatment of intracranial aneurysms, including a porous tubular member having a central portion and two ends.

As previously discussed, a significant drawback of some of the known filtering means is their tendency to become clogged. These devices need to be either cleaned or replaced to avoid significant patient complications.

As such, there is need to provide self cleaning devices, systems and methods for preventing embolic material from entering the carotid arteries supplying blood to the brain, and thus preventing emboli from occluding small intercranial arteries in the brain and preventing strokes. It would be advantageous if such devices were suitable for permanent implantation.

SUMMARY

In certain embodiments, the present invention relates to a self cleaning device comprising a first flexible filter having a first end, a second end, a first external surface, and a first filter release force, the first end configured to reside at or near a junction of at least one branch blood vessel and another blood vessel, and the second end configured to extend at least partially within the other blood vessel; and a first frame positioned at least at the first end of the first filter and configured to hold the first end of the first filter at the junction of the at least one branch blood vessel and the other blood vessel. The first external surface of the first filter is configured to temporarily trap at least some of the embolic material flowing about the junction of the at least one branch blood vessel and the other blood vessel as a result of blood inflow through the first filter, and where the first external surface of the filter is further configured to expel the trapped embolic material into the other blood vessel as a result of the first filter release force. The first filter may include pores. The pores may range in size from about 0.02 mm to about 0.5 mm. The pores may form a taper as a result of the first flexible filter release force. The first filter may comprise a material selected from the group consisting of polyester, polytetrafluoroethylene, polyurethane, and silicone rubbers. The first filter may comprise pleats. The device may also include at least one supporting wire, the supporting wire comprising two support elements and at least one loop. The support elements may comprise nitinol. The first filter, the first frame, or both may comprise at least one agent to prevent thrombogenesis and or to enhance endothelialization and or to prevent or inhibit the growth of smooth muscle or other cells onto the surface of the first filter, the first frame, or both. The agent may be selected from the group consisting of endothelial cells derived from the subject prior to installation of the device in the subject, nitric oxide emitter compound, an antibody to circulating progenitor cells, at least one fibronectin-derived low-molecular-weight peptide fragment, Resten-NG, AVI-4126, and AVI-5126. The at least one branch blood vessel may be the brachiocephalic artery and the other blood vessel may be the aorta. The device may also include a tubular member configured to hold at least the first filter. The tubular member may be a stent. The device may also include a second flexible filter, the second filter having a first end, a second end, a second external surface, and a second release force, the first end of the second filter configured to reside at or near a junction of the at least one branch blood vessel and the other blood vessel, and the second end of the second filter configured to extend at least partially within the other blood vessel; and a second frame positioned at least at the first end of the second filter and configured to hold the first end of the second filter at the junction of the at least one branch blood vessel and the other blood vessel. The second external surface of the second filter may be configured to temporarily trap at least some of the embolic material flowing about the junction of the at least one branch blood vessel and the other blood vessel as a result of blood inflow though the second filter, and wherein the second external surface of the filter may be further configured to expel the trapped embolic material into the other blood vessel as a result of a second filter release force. The at least one branch blood vessel may include brachiocephalic artery and left common carotid artery, and the other blood vessel may be aorta. The device may also include a tubular member configured to hold at least the first filter and the second filter.

In another embodiment, the invention relates to a method for preventing embolic stroke in a subject. The method includes placing the device described herein at the junction of the at least one branch blood vessel and the other blood vessel.

In yet another embodiment, the invention relates to a system. The system includes a self cleaning flexible filter having a first end, a second end, an external surface, and a filter release force, the first end configured to reside at or near a junction of at least one branch blood vessel and another blood vessel, and the second end configured to extend at least partially within the other blood vessel, where the external surface of the filter is configured to temporarily trap at least some of the embolic material flowing about the junction as a result of blood inflow through the filter, and wherein the external surface of the filter is further configured to expel the trapped embolic material into the other blood vessel as a results of the filter release force; a frame positioned at least at the first end of the filter and configured to hold the first end of the filter at the junction; a tubular member configured to hold the filter, the frame or both; and at least two support elements.

In yet another embodiment, the invention relates to a method of preventing embolic material flowing about a junction of at least one branch blood vessel and another blood vessel from entering the at least one branch blood vessel. The method includes placing at the junction a device comprising a self cleaning flexible filter, the flexible filter having a first end, a second end, an external surface, and a filter release force, the first end configured to reside at or near the junction, and the second end configured to extend at least partially within the other blood vessel, and a frame positioned at least at the first end of the filter and configured to hold the first end of the filter at the junction. The method also includes temporarily trapping on the external surface of the filter at least some of the embolic material flowing about the junction as a result of blood inflow though the filter; and via a release force expelling the embolic material from the external surface of the filter into the other blood vessel. The method may further include placing a tubular member at or near the junction, the tubular member being configured to hold the filter. The device may be permanently placed at the junction.

Other devices, systems, methods, features and advantages will be, or will become, apparent to one with skill in the art upon examination of the following figures and detailed description. It is intended that all such additional systems, methods, features and advantages be included within this description, be within the scope of the invention, and be protected by the following claims.

BRIEF DESCRIPTION OF THE DRAWINGS

The devices, systems and methods may be better understood with reference to the following drawings and description. The components in the figures are not necessarily to scale, emphasis instead being placed upon illustrating the principles of the invention. Moreover, in the figures, like referenced numerals designate corresponding parts throughout the different views.

DETAILED DESCRIPTION OF THE DRAWINGS AND THE PRESENTLY PREFERRED EMBODIMENTS

Figure 1:
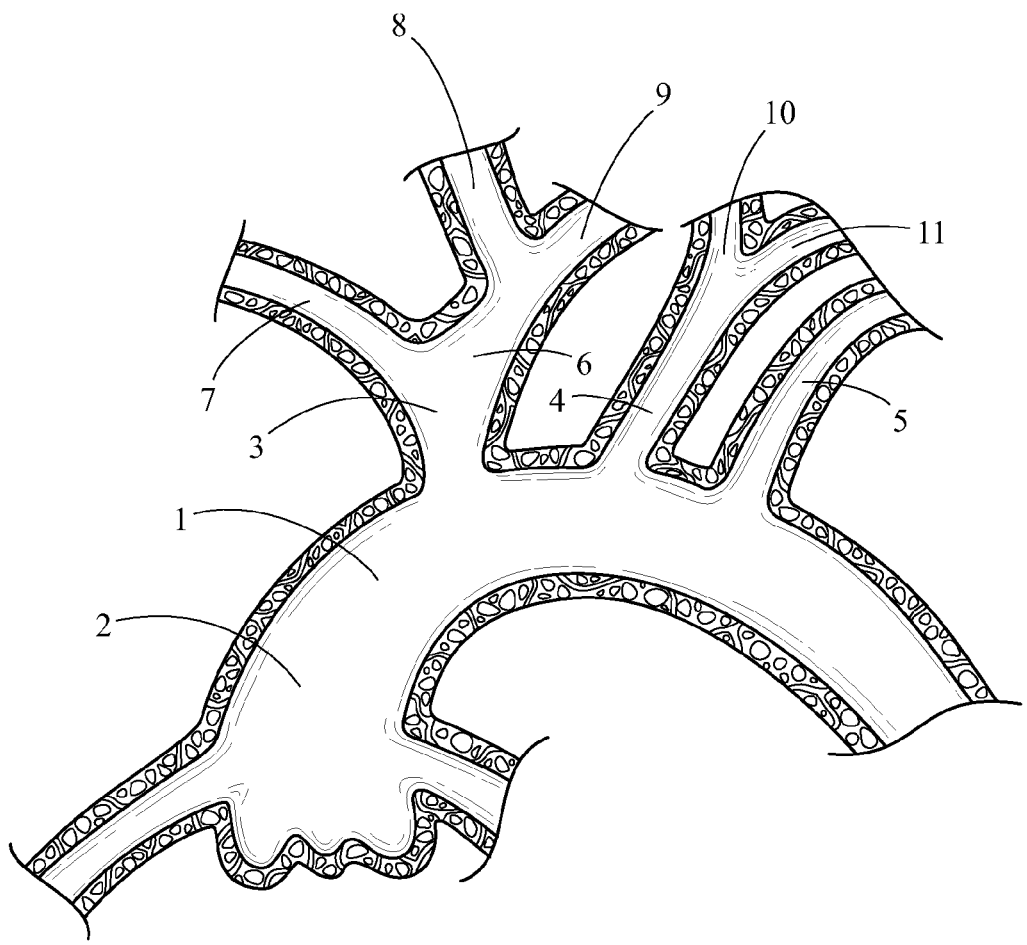
FIG. 1 is a schematic illustration of the arch of the aorta and branch vessels.

The present invention relates to medical devices, systems, and methods. More particularly, the present invention relates to devices, systems and methods for preventing the embolic material that is flowing about a junction of at least two blood vessels from entering a specified blood vessel. Specifically, the devices, systems and methods may be for preventing embolic material flowing about a junction of aorta and brachiocephalic and carotid arteries that supply blood to the brain from entering these blood vessels. These devices and systems are self cleaning and suitable for permanent implantation without the need to replace or clean the devices and systems.

The device generally includes a filter, a frame, and optionally a stent-like tube element that may be temporarily or permanently placed in the arch of the patient's aorta and that may serve as a platform or holder for the filter. One or more filters may be positioned at the junction of the aorta and its branches to filter all of the blood that enters the head (cranium) with or without the tube element.

Preferably, the filter of the device is configured (either structurally or by using a specific filter material) to include a release force. The embolic material that becomes temporarily trapped on the surface of the filter that the embolic material comes in contact with (i.e., the external surface of the filter) as a result of the blood flow from aorta through the filter and into the brachiocephalic and/or left common carotid arteries may then be expelled back into the aorta. The specific configurations of the filter that provide for the release force may include pleats (circumferential or longitudinal), specific pore shapes, and other configurations. These configurations allow the filter to be self cleaning and suitable for permanent implantation without the need for a periodic cleaning or replacing of the filter.

Also, specific placement of the filter at the junction of the aorta and its branch blood vessels and or coating at least a portion of the device with agents to prevent thrombogenesis and or to enhance endothelialization and or to prevent or inhibit the growth of smooth muscle or other cells on the device may further enhance the self-cleaning and release force properties of the filter.

Definitions:

It should be noted that references to "an", "one", or "various" embodiments in this disclosure are not necessarily to the same embodiment, and such references contemplate more than one embodiment.

As used herein the terms "comprise(s)," "include(s)," "having," "has," "can," "contain(s)," and variants thereof, are intended to be open-ended transitional phrases, terms, or words that do not preclude the possibility of additional acts or structures. The present invention also contemplates other embodiments "comprising," "consisting of" and "consisting essentially of," the embodiments or elements presented herein, whether explicitly set forth or not.

The recitation of "about" or "substantially" used with reference to a quantity, such as pore size, includes variations in the recited quantity that are equivalent to the quantity recited, for instance an amount that is insubstantially different from a recited quantity for an intended purpose or function.

The term "antibody" refers to an immunoglobulin, derivatives thereof that maintain specific binding ability, and proteins having a binding domain that is homologous or largely homologous to an immunoglobulin binding domain. These proteins may be derived from natural sources, or partly or wholly synthetically produced. An antibody may be monoclonal or polyclonal. The antibody may be a member of any immunoglobulin class, including any of the human classes: IgG, IgM, IgA, IgD, and IgE. In certain embodiments, antibodies used with the devices, systems or methods described herein are derivatives of the IgG class.

The term "bioabsorbable" is used herein to refer to materials selected to dissipate upon implantation within a body, independent of which mechanisms by which dissipation can occur, such as dissolution, degradation, absorption and excretion. The terms "bioabsorbable," "bioresorbable," or "biodegradable" are used synonymously herein, unless otherwise specified, to refer to the ability of the material or its degradation products to be removed by biological events, such as by fluid transport away from the site of implantation or by cellular activity (e.g., phagocytosis). Only the term "bioabsorbable" will be used in the following description to encompass absorbable, bioabsorbable, and biodegradable, without implying the exclusion of the other classes of materials.

As used herein, recitation of a "non-bioabsorbable" material refers to a material, such as a polymer or copolymer, which remains in the body without substantial bioabsorption.

The terms "bifurcation" or "junction" refer to an area in vasculature where a blood vessel either divides or bifurcates into at least two blood vessels, or where at least one branch blood vessel forms off the main blood vessel.

As used herein, the term "body vessel" means any body passage lumen that conducts fluid, including but not limited to blood vessels, esophageal, intestinal, billiary, urethral and ureteral passages.

The term "branch blood vessel" refers to a blood vessel that branches off of a main blood vessel. For example, the brachiocephalic and left common carotid arteries are branch blood vessels which originate from or branch off of the aorta.

The term "catheter" refers to a tube that is inserted into a blood vessel to access the vessel. Catheter includes catheter per se, or a catheter set including a catheter, needle, guide wire, introducer sheath and other suitable medical devices. Catheter may be a microcatheter.

The term "coating," as used herein and unless otherwise indicated, refers generally to a material or agent attached to a medical device. A coating can include material covering any portion of a medical device or the entire device, and can be configured as one or more coating layers. A coating can have a substantially constant or a varied thickness and composition. Coatings can be adhered to any portion of a medical device surface, including the lateral surface, the lumenal surface, the ablumenal surface, or any portions or combinations thereof, or the entire device.

As used herein, the phrase "controlled release" refers to the release of the coating agent at a predetermined rate. A controlled release may be characterized by a drug elution profile, which shows the measured rate that the agent is removed from an agent-coated device in a given solvent environment as a function of time. A controlled release does not preclude an initial burst release associated with the deployment of the medical device, because in some embodiments of the invention an initial burst, followed by a more gradual subsequent release, may be desirable. The release may be a gradient release in which the concentration of the coating agent released varies over time or a steady state release in which the coating agent is released in equal amounts over a certain period of time (with or without an initial burst release).

When coated, the coating may be present on any portion of a surface of the device. In one embodiment, the surface is the inner surface (for example, a surface that is in contact with blood). In another embodiment, the surface is the outer surface (for example, a surface that is in contact with a blood vessel). In one embodiment, the layer covers at least about 10% of the surface. In another embodiment, the layer covers at least about 20% of the surface. In another embodiment, the layer covers at least about 30% of the surface. In another embodiment, the layer covers at least about 40% of the surface. In another embodiment, the layer covers at least about 50% of the surface. In another embodiment, the layer covers at least about 60% of the surface. In another embodiment, the layer covers at least about 70% of the surface. In another embodiment, the layer covers at least about 80% of the surface. In another embodiment, the layer covers at least about 90% of the surface. In another embodiment, the layer covers about 100% of the surface. In yet other instances, the layer covers from about 10% to about 100% of the surface.

As used herein, the term "preventing" includes inhibiting the embolic material from entering a specified blood vessel, such as a branch blood vessel.

The term "distal" refers to an area furthest from a point of reference such as an origin or a point of attachment.

The term "proximal" refers to an area nearer to a point of reference such as an origin or a point of attachment.

The term "incorporated" means that the agents are coated, adsorbed, placed, deposited, attached, impregnated, mixed, or otherwise incorporated into at least a part of the device and any additional layers, if present, by methods known in the art.

As used herein, the term "implantable" refers to an ability of a medical device to be positioned at a location within a body for any suitable period of time, such as within a body vessel. Furthermore, the terms "implantation" and "implanted" refer to the positioning of a medical device at a location within a body, such as within a body vessel. Implantable medical devices can be configured for transient placement within a body vessel during a medical intervention (e.g., seconds, minutes, hours), or to remain in a body vessel for a prolonged period of time after an implantation procedure (e.g., weeks or months or years). Implantable medical devices can include devices configured for bioabsorption within a body during a prolonged period of time.

As used herein, "endolumenal" or "translumenal" refer to a device adapted for placement within a body vessel by procedures wherein the prosthesis is advanced within and through the lumen of a body vessel from a remote location to a target site within the body vessel. In vascular procedures, a medical device can typically be introduced "endovascularly" using a catheter over a wire guide under fluoroscopic guidance. The catheters and wire guides may be introduced through conventional access sites to the vascular system.

The term "endothelialization" refers to a cellular process resulting in ingrowth of the endothelial cells onto a device.

As used herein, the term "patient" or "subject" means an animal (e.g., cow, horse, sheep, pig, chicken, turkey, quail, cat, dog, mouse, rat, rabbit or guinea pig), preferably a mammal such as a non-primate or a primate (e.g., monkey or human), most preferably a human.

The term "pharmaceutically acceptable carrier" or "carrier" includes any material which, when combined with a coating agent, allows the agent to retain biological activity, such as the ability to prevent thrombogenesis, and is non-reactive with the subject's immune system. Examples include, but are not limited to, any of the standard pharmaceutical carriers such as a phosphate buffered saline solution, water, emulsions such as oil/water emulsions, various polymer carrier materials, and various types of wetting agents. Compositions comprising such carriers are formulated by well known conventional methods (see, for example, Remington's Pharmaceutical Sciences, Chapter 43, 14th Ed., Mack Publishing Co., Easton, Pa.).

The term "progenitor cells" refers to precursor stem cells that are unspecialized or have partial characteristics of specialized cells that are capable of undergoing cell division.

The term "stent" refers to any structure that is used to hold tissue in place within a body, including an interior portion of a blood vessel, lymph vessel, ureter, bile duct or portion of the alimentary canal. A stent may be useful for opening up blood vessels, such as for example, an artery, vein or capillary thereby improving blood flow; keeping an artery, vein or capillary open; sealing any tears or openings in an artery, vein or capillary; preventing an artery, vein or capillary wall from collapsing or closing off again; or preventing small pieces of plaque from breaking off. In certain instances, the stent may be a stent graft.

The term "temporary" when referring to placement of a medical device in a blood vessel means that the device is placed in the blood vessel for a relatively short period of time. For example, the device may be placed in a blood vessel for a few minutes to few hours (for example, length of a medical procedure). The term "temporary" when referring to a medical device also may mean that the device is placed in a blood vessel for longer periods of time (e.g., days, weeks or months) and later removed from the blood vessel.

The term "permanent" refers to a medical device which may be placed in a blood vessel and will remain in the blood vessel for a long period of time (e.g., months, years) and preferably for the remainder of the patient's life.

The terms "agent" and "compound" refers to any pharmaceutical (drug, chemical, polymer, etc.) or biological agent (such as an antibody, polypeptide, polynucleotide, etc.), or compositions thereof that may be used with the device of this invention to prevent thrombogenesis and or to enhance endothelialization and or to prevent or inhibit the growth of smooth muscle or other cells on the device. Some exemplary agents are discussed in more detail below.

The term "effective amount" refers to a dose of an agent or compound that effectively prevents thrombogenesis and or enhance endothelialization, but does not cause undesirable or intolerable side effects.

The terms "thrombogenesis" or "thrombosis" refer to formation, development, or presence of a thrombus. A thrombus may form whenever the flow of blood in the arteries or the veins is impeded. If the thrombus detaches itself from the wall and is carried along by the bloodstream, the thrombus is called an "embolus" or "embolic material."

The terms "embolus" or "embolic material" or "filtrate" refer to a clot or foreign material which has been brought to its site of lodgment by the blood current. The obstructing material is most often a blood clot (i.e., thrombus), but may be a fat globule (due to atherosclerosis), air bubble, piece of tissue, e.g., degenerated intervertebral disk, or clump of bacteria. The terms "embolus," "embolic material," and "filtrate" may be used interchangeably.

The term "self cleaning" refers to an inherent ability of the medical device to clean itself or be cleaned by endogenous forces or actions without need for periodic cleaning by a physician or removal of the device from the vasculature of the patient.

The term "expelling" refers to an ability of the device to force out or eject any material, such as embolic material that may become temporarily trapped on the device as a result of a blood inflow thought the device. Expelling may be by and includes: expelling per se, vibrating, flowing, waving, contracting from expanded configuration to folded or contracted configuration, bowing, bending outwardly and inwardly, folding in and out, flapping, flexing, forcing out, vibrating, oscillating, etc.

The terms "filter" and "filter material" refer to at least a portion of a device that is configured to temporarily trap at least some of the embolic material flowing about a junction of at least one branch blood vessel and another blood vessel as a result of blood inflow though the device; and also configured to expel the trapped embolic material into the blood stream, such as aortic blood stream, as a result of the filter or filter material release force. The terms "filter" and "filter material" may be used interchangeably.

The term "release force" refers to an inherent property of the filter or the filter material. Specifically, it is the force that is imparted on the filtrate by the motion of the filter or the filter material in the direction of the aorta lumen. It also comprises the force that is imparted on the filtrate by the flowing aortic blood with which it comes in contact. If either or both of these forces acting on the filtrate are sufficient, at least some of the filtrate will leave the filter or the filter material and enter the aortic blood stream.

The term "external surface" refers to a surface of the device and especially of the filter or the filter material that is facing the incoming blood inflow through the device. The external surface of the filter is configured to temporarily trap the embolic material on the external surface per se, in the external surface, and or in the pores of the filter and or the filter material.

Blood to the brain hemispheres is in majority supplied by two arteries, left and right common carotid arteries, each of which branches off or bifurcates into internal carotid artery and external carotid artery. Blood to the brain stem is supplied by two vertebral arteries.

FIG. 1 illustrates the arch of aorta 1 and blood vessels that branch off of the arch of aorta. The aorta 2 is the main trunk of a series of vessels which convey the oxygenated blood to the tissues of the body for their nutrition. It commences at the upper part of the left ventricle and, after ascending for a short distance, arches backward and to the left side, over the root of the left lung; it then descends within the thorax on the left side of the vertebral column, passes into the abdominal cavity though the aortic hiatus in the diaphragm, and ends, considerably diminished in size, opposite the lower border of the fourth lumbar vertebra by dividing into right and left common iliac arteries.

There are three branches (i.e., branch blood vessels) given off from the arch of the aorta 2: brachiocephalic 3 (i.e., innominate), left common carotid 4 and the left subclavian arteries 5. The brachiocephalic artery 3 is the largest branch of the arch of the aorta 1 and it is from 4 to 5 cm in length. It divides into the right common carotid 6 and right subclavian arteries 7. The right common carotid artery 6 then branches off or bifurcates into the internal carotid artery 8 and external carotid artery 9, the external carotid artery supplying the exterior of the head, the face, and the greater part of the neck and the internal carotid, supplying to a great extent the parts within the cranial and orbital cavities. The left common carotid artery also divides into an internal carotid artery 10 and external carotid artery 11, the external carotid artery supplying the exterior of the head, the face, and the greater part of the neck and the internal carotid, supplying to a great extent the parts within the cranial and orbital cavities.

Figure 2A:
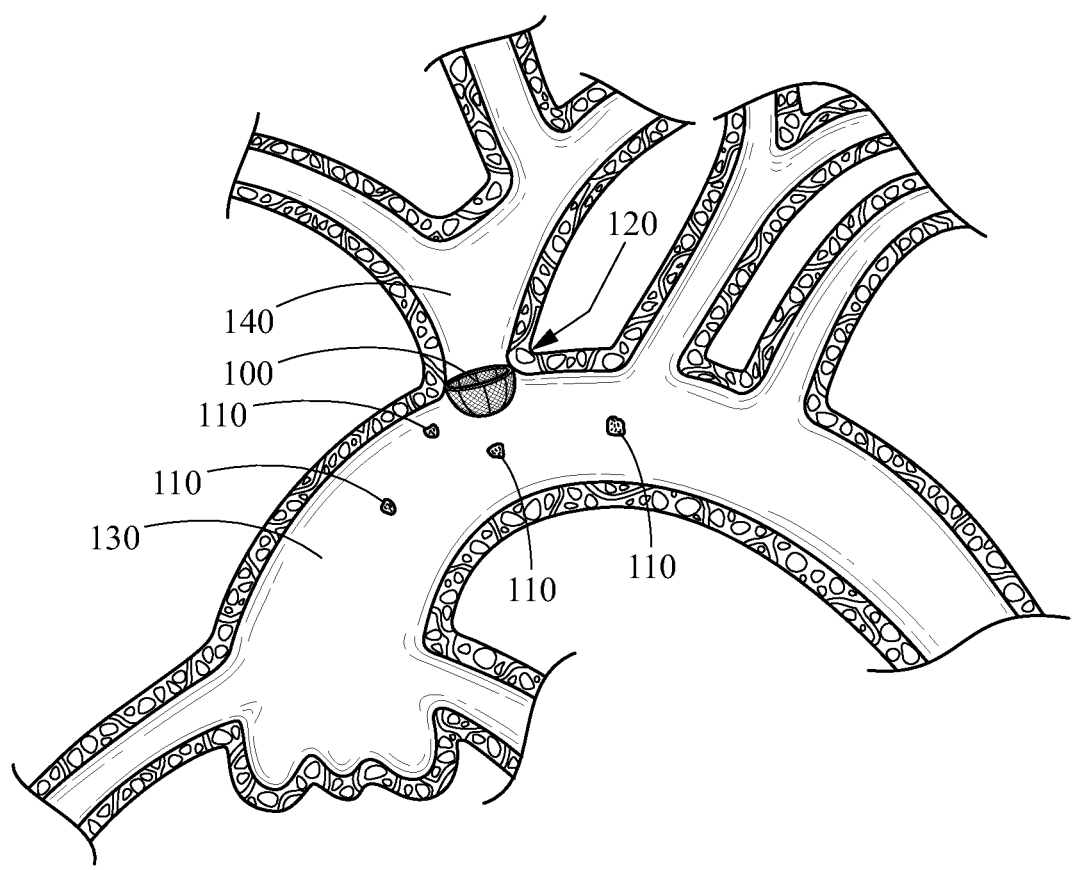
FIGS. 2A-2B are schematic illustrations of an exemplary device of this invention placed at a junction of two blood vessels.
Figure 2B:
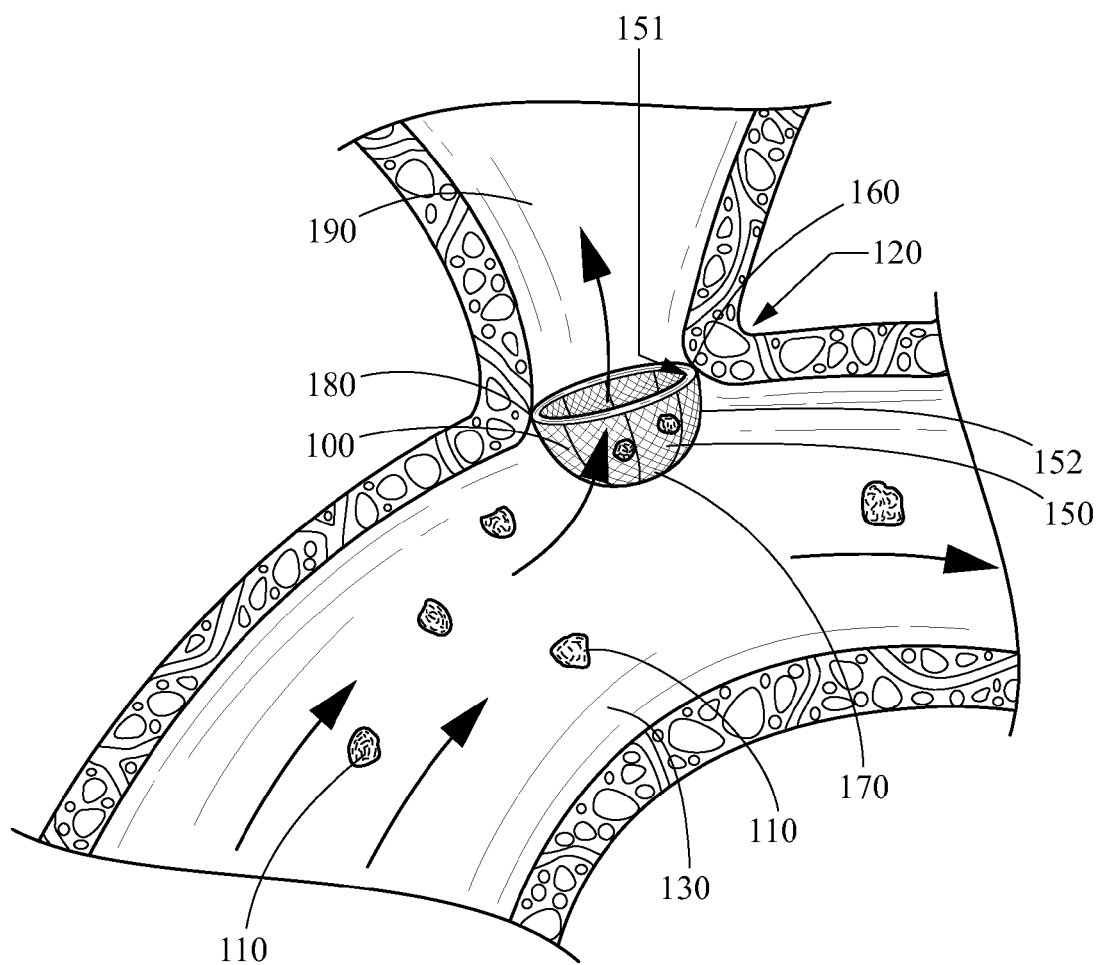
Figure 3A:
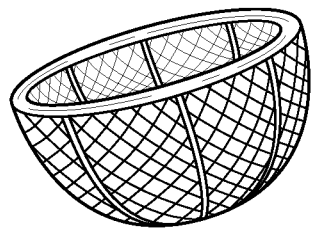
FIGS. 3A-3E are schematic illustrations of various exemplary shapes of the filter.
Figure 3B:
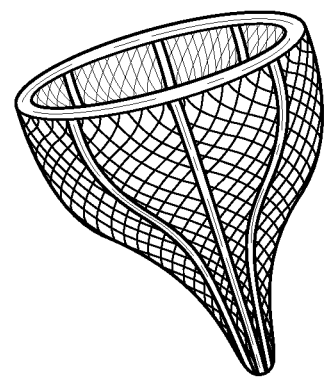
Figure 3C:
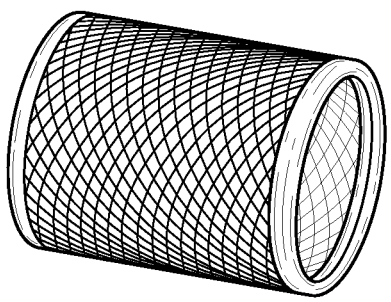
Figure 3D:
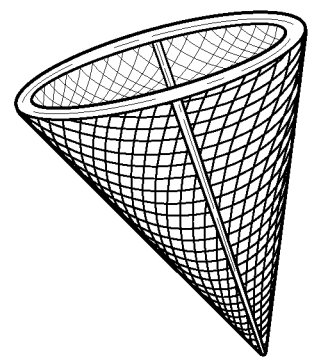
Figure 3E:
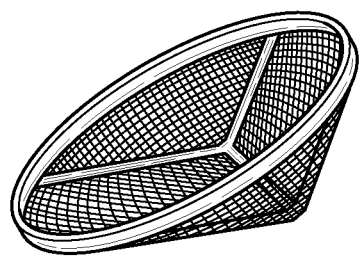

As shown in FIGS. 2A and 2B, the self cleaning device 100 is for expelling embolic material 110 that may become temporarily trapped on the exterior surface of the device 100 as a result of blood inflow though the device and for diverting the material away from the above branch arteries and back into the aortic blood stream. The device is placed at or near a junction 120 of at least one branch blood vessel 140 and another blood vessel 130, and includes a flexible filter 150 having a first end 160 and a second end 170, an internal surface 151 and an external surface 152 (i.e., the surface of the filter that faces the blood vessel 130), and a filter release force. The first end 160 may reside at or near the junction 120 of the branch vessel 140 and the other vessel 130. The second end 170 may extend at least partially within the other blood vessel 130. The device may include a frame 180 positioned at least at the first end 160 of the filter 150 and to hold the first end 160 of the filter 150 at the junction 120.

In operation, the external surface 152 of the filter 150 temporarily traps at least some of the embolic material 110 flowing about the junction 120 as a result of blood inflow (arrows) through the filter 150. The filter 150 has a release force in response to blood inflow though the device. The release force causes the filter 150 to expel or release the temporarily trapped embolic material 110 into the blood vessel 130 and back into the aortic blood stream, thereby diverting the material away from the branch blood vessels leading to the brain. In certain embodiments, the filter will move outwardly and inwardly with respect to the aorta lumen as the blood inflow though the device decreases and increases, respectively.

Figure 4A:
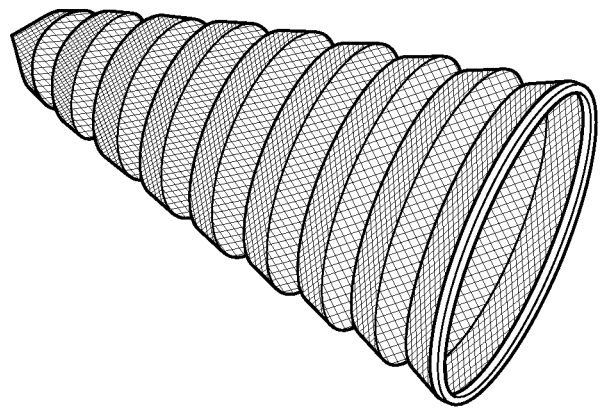
FIGS. 4A-4C are schematic illustrations of various exemplary configurations of the filter.
Figure 4B:
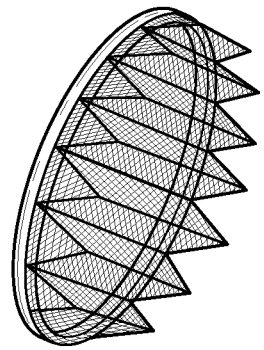
Figure 4C:
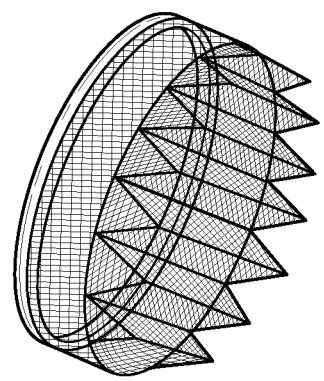
Figure 18:
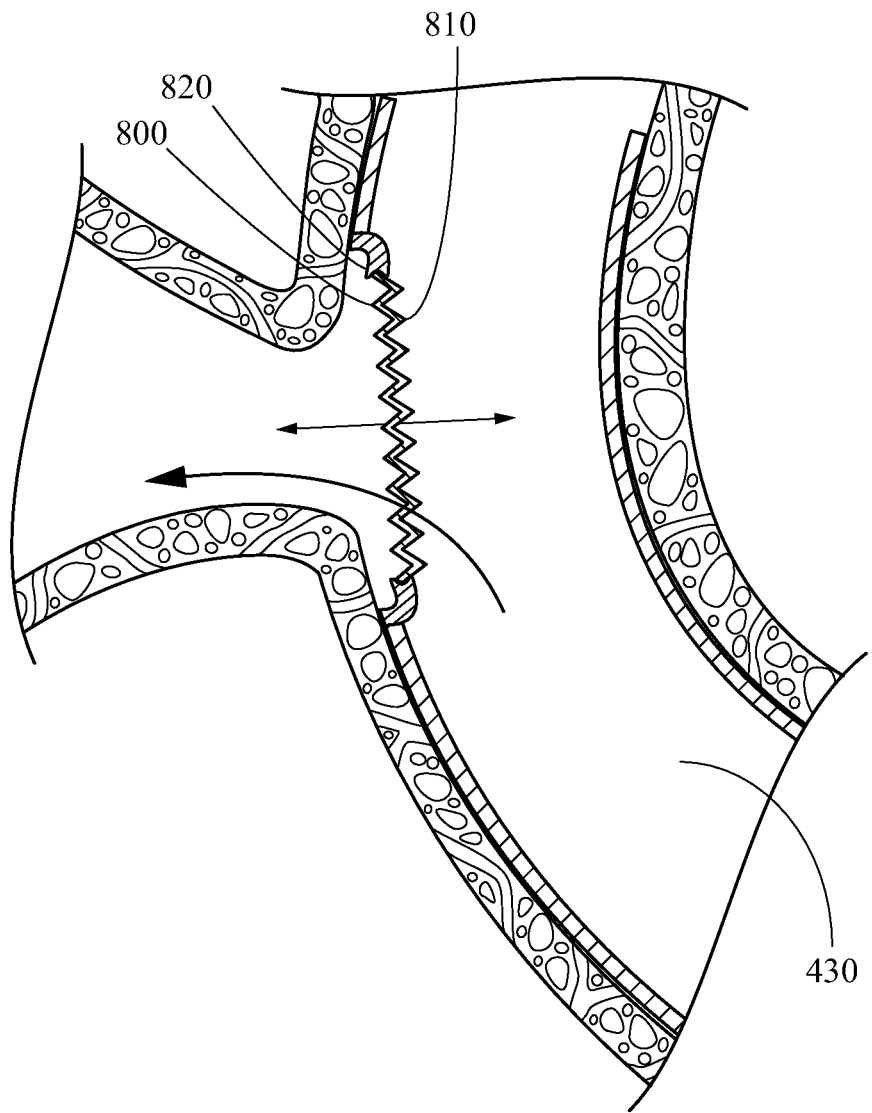
FIG. 18 depicts yet another example of a device of this invention.

The filter may be a porous membrane. The first end 160 of the porous filter may be configured to hold the first end 160 of the porous filter 150 at the junction 120 of at least one branch blood vessel 190 and another blood vessel 130. The filter 150, when expanded as shown in FIG. 3A-3E, may assume a specified expanded shape/configuration. For example, the filter may assume a shape of a dome or hemisphere (FIG. 3A), a funnel (FIG. 3B), a cylinder (FIG. 3C), a cone (FIG. 3D), a pyramid (FIG. 3E), or a flat corrugated or pleated sheet (FIG. 18). Other suitable shapes are also contemplated. The filter may include pleated rings or may be folded (circumferentially and/or longitudinally), as shown in FIGS. 4A-4C.

The filters also may have various diameters to at least match and preferably exceed the diameter of at least one inlet to the branch blood vessel, such as the brachiocephalic and/or the left carotid arteries. For example, a filter having a dome shape would preferably have a dome height of between about 0.5 cm and about 3 cm.

Figure 5A:
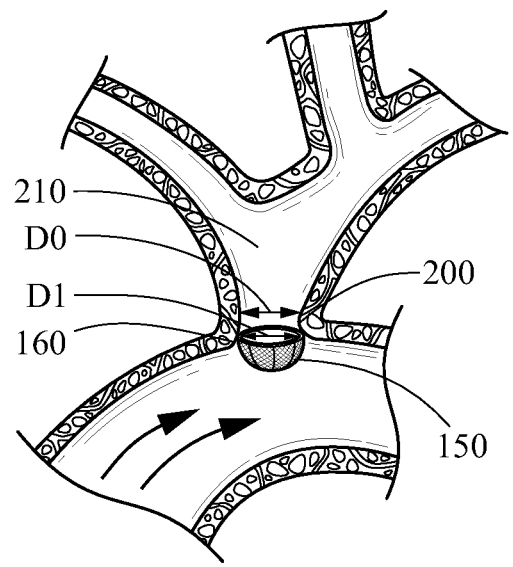
FIGS. 5A-5D are schematic illustrations of further exemplary configurations of the device.
Figure 5B:
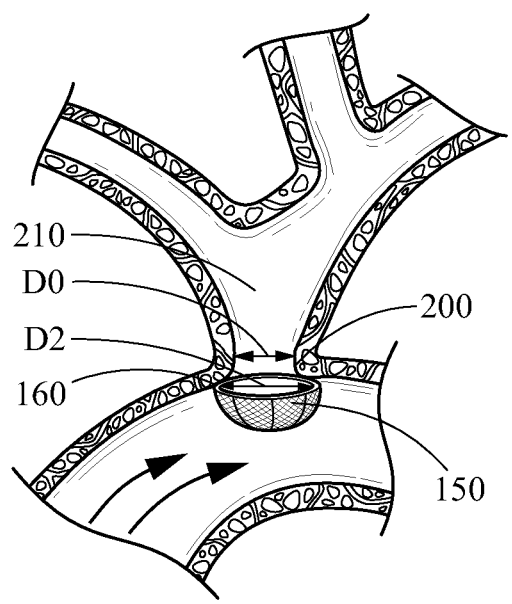
Figure 5C:
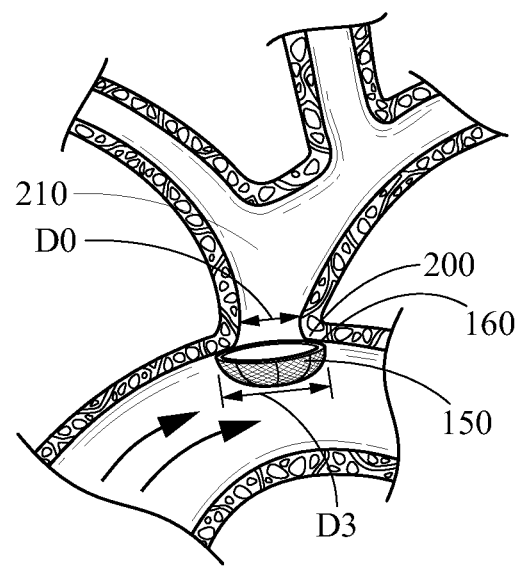
Figure 5D:
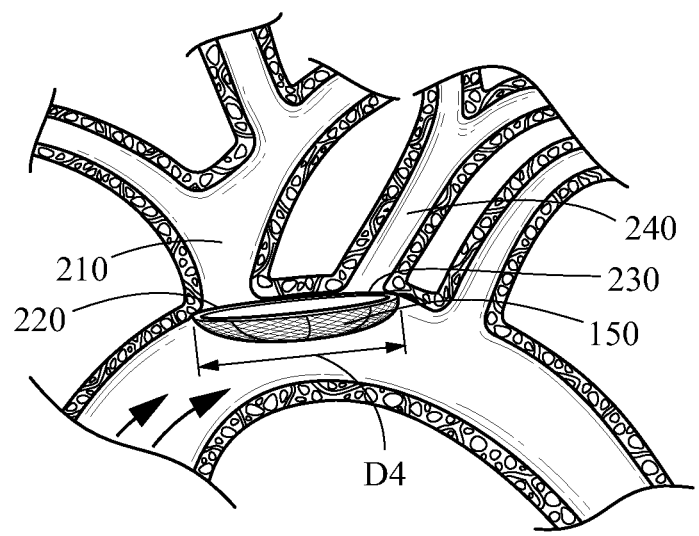

FIGS. 5A-5D illustrate exemplary filters 150 with varying diameters D1-D4 in relationship to the diameter D0 of the inlet 200 of the blood vessel where the filter 150 will be placed. The diameter may be adjustable. The diameter D1 of the filter's opening at the first end 160 may be the same size as the diameter D0 of the inlet 200 to the branch blood vessel 210, as shown in FIG. 5A. In certain instances, the diameter D2 of the filter's opening at the first end may be slightly larger than the diameter D0 of the inlet 200 to the branch blood vessel 210, as shown in FIG. 5B. In yet other embodiments, the diameter D3 of the filter's opening at the first end may be significantly larger than the diameter D0 of the inlet 200 to the branch blood vessel 210 (FIG. 5C). In yet other instances, the diameter D4 of the filter's opening at the first end may be sufficiently large to cover the inlets 220 and 230 to the branch blood vessels 210 and 240, as shown in FIG. 5D.

The filter 150 may be a porous filter and may be made from various suitable materials (i.e., filter material) for intended use. Preferably, the flexible filter is made from material that would allow the filter, when the filter is in an expanded configuration, to contract from its expanded position, flex, vibrate, oscillate, bow, bend outwardly and inwardly, fold in and out, flap, etc.

For example, the filter may be made of fine woven wire (made from biocompatible metals or other metallic materials) made into a net-like device having construction suitable to contract from the expanded position in which it is deployed.

Suitable metallic materials include stainless steels (e.g., 316, 316L, 304L or 304); nickel-titanium alloys including shape memory or superelastic types (e.g., nitinol or elastinite); noble metals including platinum, gold or palladium; refractory metals including tantalum, tungsten, molybdenum or rhenium; stainless steels alloyed with noble and/or refractory metals; silver; rhodium; inconel; iridium; niobium; titanium; magnesium; amorphous metals; plastically deformable metals (e.g., tantalum); nickel-based alloys (e.g., including platinum, gold and/or tantalum alloys); iron-based alloys (e.g., including platinum, gold and/or tantalum alloys); cobalt-based alloys (e.g., including platinum, gold and/or tantalum alloys); cobalt-chrome alloys (e.g., elgiloy); cobalt-chromium-nickel alloys (e.g., phynox); alloys of cobalt, nickel, chromium and molybdenum (e.g., MP35N or MP20N); cobalt-chromium-vanadium alloys; cobalt-chromium-tungsten alloys; platinum-iridium alloys; platinum-tungsten alloys; magnesium alloys; titanium alloys (e.g., TiC, TiN); tantalum alloys (e.g., TaC, TaN); L605; and magnetic ferrite.

If a wire is used to form the filter, the preferred diameter of the wire should be in the range of from about 10 μm to about 250 μm.

The filter also may be constructed from other materials, including elastomeric materials, such as or polyethylene terephthalate (e.g., dacron or mylar); expanded fluoropolymers (e.g., polytetrafluoroethylene (PTFE)); polyurethane; polyester, polyurethane (THORALON (THORATEC, Pleasanton, Calif.)), polyethylene, polypropylene and polytetrafluoroethylene; or a porous biostable material, such as parylene, or a poly(alkyl)methacrylate (e.g., poly(butyl) methacrylate); a woven or non-woven fabric, such as Dacron®; and silicone rubbers. Some preferred filter materials include polymethyl pentene, ethylene-chlorotrifluoroethylene, biaxially stressed polypropylene, or other polymers, such as KYNAR (polyvinyl difluoride), THERMALUX (polysulfone), and PET (polyethylene terephthalate). Although elastomeric materials are preferred, suitable non-elastomeric materials may also be used.

Biological tissues may also be suitable for use as the filter material may include those appropriate for implantation into humans or animals. Tissues can be human or non-human (e.g. bovine, porcine or non-human primate) in origin. The tissues can be fresh or cryopreserved by methods known in the art. In either case, the tissue may be denatured or decellularized prior to any fixation to avoid any inflammatory responses. Methods of decellularization of tissue are known in the art; see e.g., U.S. Pat. No. 7,318,998. Tissues that may be suitable for use as filter material may include heart valve leaflets, tendons, ligaments, bone, facia, arteries, veins, diaphragm, pericardium, umbilical cords, dura mater, tympanic membranes, or the like. In certain embodiments, where the tissue is an autograft, decellularization of the tissue may not be suitable or necessary.

Figure 6A:
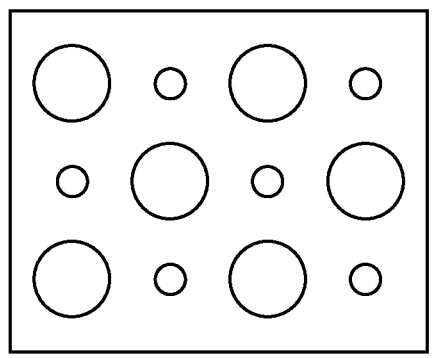
FIGS. 6A-6C are schematic illustrations of exemplary pore configurations and shapes.
Figure 6B:
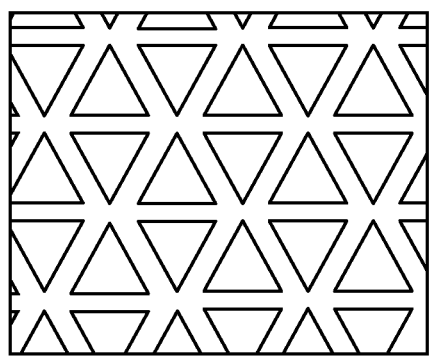

As discussed above, the filter or the filter material has pores; forming a material that is porous. The porous filter is formed to have or of material having a pore size which obstructs objects about 5 mm in diameter or less, more preferably about 3 mm in diameter, more preferably less than about 3 mm in diameter, more preferably about 2.75 mm, more preferably less than about 2.5 mm, more preferably less than about 2 mm, more preferably less than about 1.5 mm, more preferably less than about 1 mm, more preferably less than about 0.75 mm, more preferably less than about 0.5 mm, more preferably about 0.25 mm, more preferably less than about 0.1 mm, more preferably less than about 0.075 mm, more preferably less than about 0.05 mm, more preferably less than about 0.025 mm, and more preferably less than about 0.02 mm, and down to sizes just larger than or about the size of a white blood cell and or a red blood cell. In certain embodiments, the pore size ranges from about 0.02 mm to about 0.200 mm. In one preferred embodiment, the pore size may be 0.15 mm. It will be understood that for a given pore size that blocks particles of a certain size as stated above, that pore size will block most particles larger than that size as well, depending on their shape, elasticity, and other properties. It should also be understood that the necessary pore size is a function of blood throughput, surface area of the filter, and the pressure on the proximal and distal side of the filter. The pores of the porous filter are preferably round (FIG. 6A) but may be other shapes (FIG. 6B). Pores may also be cylindrical holes.

Figure 6C:
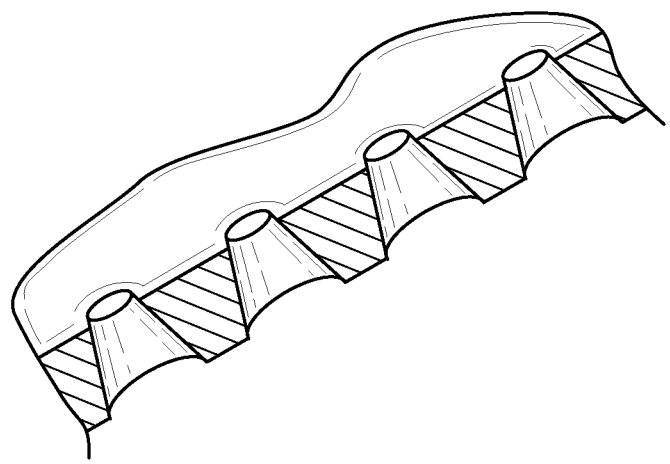
Figure 6D:
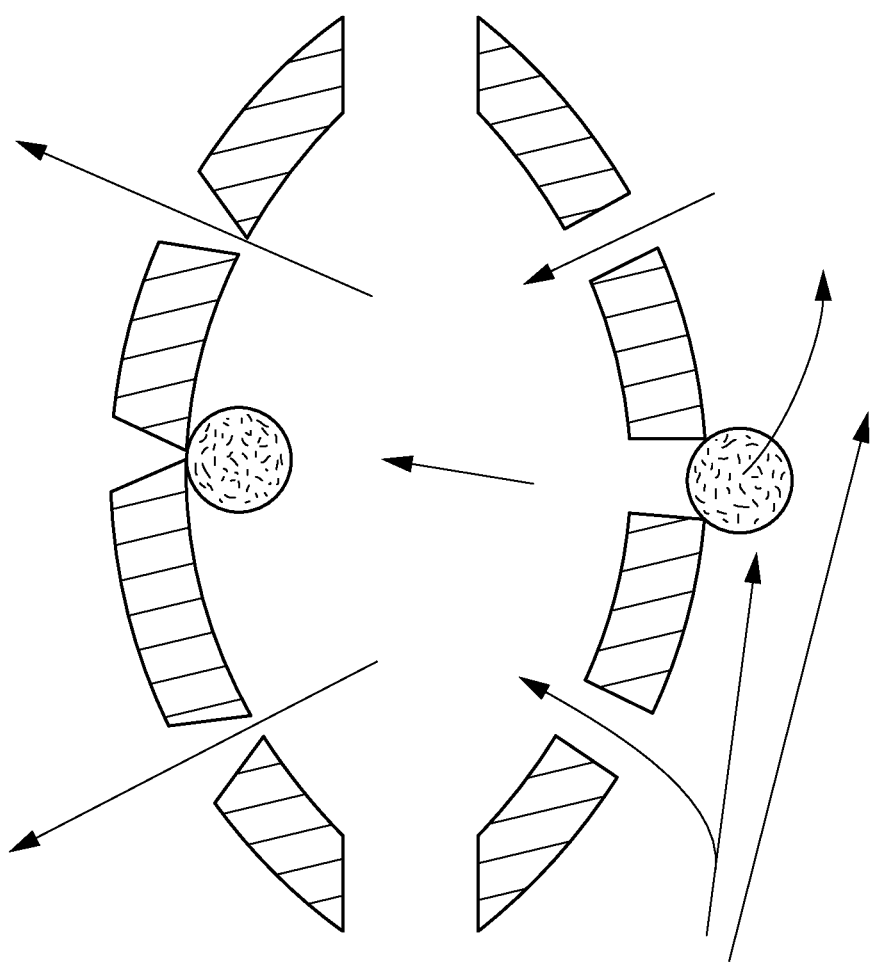
FIG. 6D illustrates exemplary filter cleaning mechanism.

The pores from the external surface to the internal surface of the filter may be tapered as shown for example, in FIG. 6C due to the filter being configured to flex. The ability of the pores to change diameter when the filter element flexes allows the pores to temporarily trap and then expel any or at least some of the embolic material that flows about a junction of the blood vessels. As illustrated in FIG. 6D, with the blood inflow (systolic blood flow into carotid artery (top of the figure) and diastolic blood flow into carotid artery (bottom of the Figure)), the pores will move between two configurations, open and less open or closed configurations. This occurs to a greater extent when the filter element is comprised of an elastomer and is thicker and to a lesser extent when it is comprised of metal or other relatively non-elastomeric material and is relatively thinner. Arrows illustrate embolus and blood movement.

Also, the filter includes an open area. The term "open area" refers to the total area on the filter surface available to the flow of blood (i.e., the total area of the pores) and is expressed as the percentage of the total area. Preferably the open area is at least 35% or higher; more preferably at least 50% or higher. In certain embodiments, the open area may be at least 75% or higher. Alternatively, the open area may be lower than 35 or 50% with the requirement that the pore size is larger, e.g., larger than 0.2 mm. The open area is important because if the filter has too low of an open area, e.g., 20%, then the flow resistance may be too high resulting in an insufficient blood flow occurring to the tissues beyond the filter, such as brain. As such, filters that have a low open area should be avoided unless the pore size of the filter is increased.

The movement of a disc-shaped filter may be amplified when it is held in radial compression by the filter frame. This causes the flat configuration of the filter to be unstable. Its stable positions will occur when it is either bowed toward the aorta blood stream or toward the cranial blood vessel lumen. Hence, more filter movement will occur with resulting more filtrate expulsion into the aortic blood stream for a given diastolic and systolic blood pressure and flow situation than if no radial compression is exerted on the filter.

Figure 8:
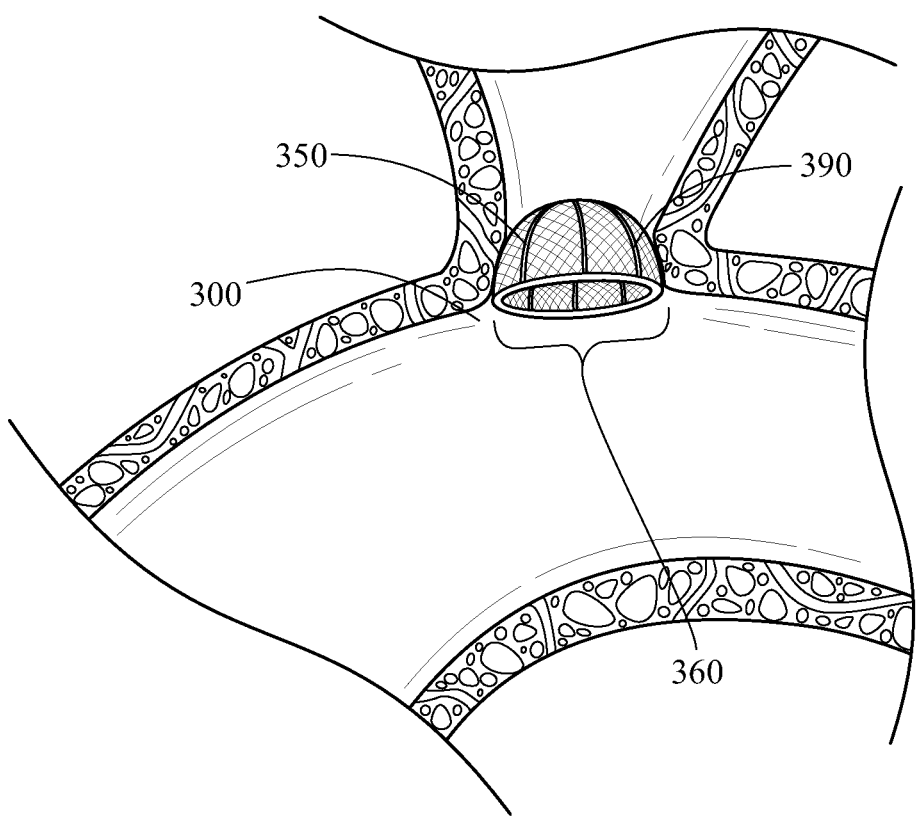
FIG. 8 is yet another schematic illustration of an exemplary device of this invention.
Figure 12:
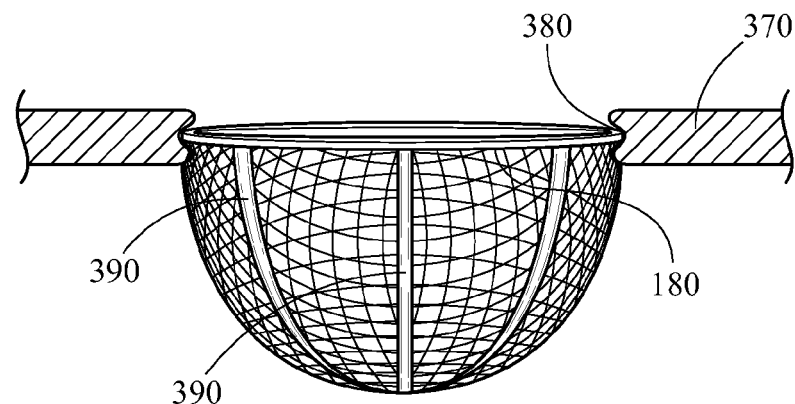
FIG. 12 is a schematic illustration of an exemplary device including a stent.

The porous filter may be made from material that is reinforced or non-reinforced. For example, as shown in FIGS. 8 and 12, the filter material may be reinforced by a filter support frame 390, which may be made from biocompatible metals, other metallic materials or other suitable materials. The metals from which such the filter support frame may be formed may include for example those provided above in reference to material that may be used to form the filter.

The first end 160 of the filter 150 may be configured to attach to the blood vessel at the junction. As such, the filter may include barbs, hooks or the like that allow for or improve or enhance the attachment of the filter to the blood vessel.

Referring back to FIG. 2B, the device also includes a filter frame (i.e., frame) 180 positioned at least at the first end 160 of the filter 150 and configured to hold the first end 160 of the filter 150 at the junction 120. In other words, the frame serves as an anchoring portion of the device. An anchoring portion is a portion of the device that firmly contacts the walls of the blood vessel to prevent accidental displacement of the device 100. The frame 180 may include barbs or hooks or the like to further aid with the attachment of the frame 180 to the blood vessel at the junction. Alternatively, in certain instances, the frame may be sutured or stapled to the wall of the blood vessel. Other alternative means of attachment of the frame to the vessel wall also may be suitable and are also contemplated.

The filter 150 may be integral with or otherwise attached to the frame 180. The frame 180 is positioned at least at the first end 160 of the filter 150 and configured to hold the first end 160 of the filter 150 at the junction 120 of at least one branch blood vessel 190 and another blood vessel 130. The frame 180 may be bonded, soldered, brazed, sutured, glued or otherwise attached to the filter. Other forms of attachment also may be suitable.

The frame 180 may be made from any suitable material. In certain instances, the frame may be formed of plastic, metal or other materials and may exhibit a multitude of configurations. The metals from which such frame may be formed may include for example, stainless steels, titanium, Nitinol, and tantalum among others. Other materials are also contemplated. In certain instances, the frame may be made from the same material as the filter. In other instances, the frame may be made from material different than the filter.

The diameter of the wire or other material that makes up the frame of the device is preferably in the range of from about 100 μm to about 500 μm.

Figure 7A:
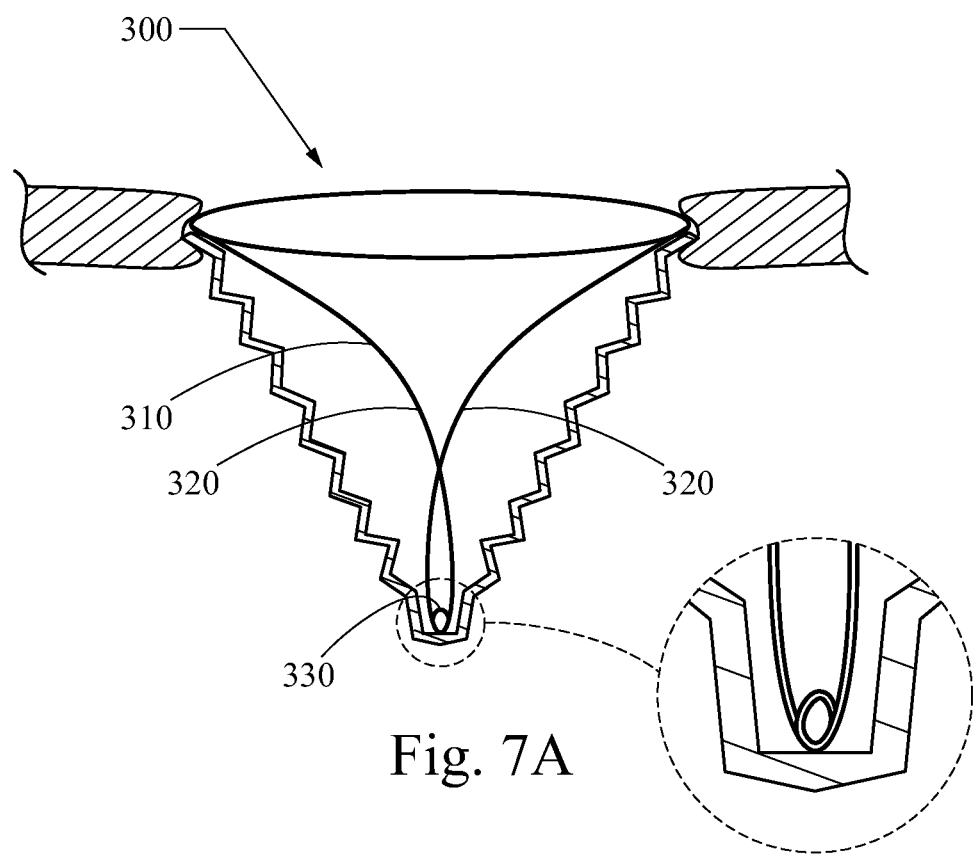
FIGS. 7A-7B are schematic illustrations of exemplary devices of this invention having varying numbers of support elements.
Figure 7B:
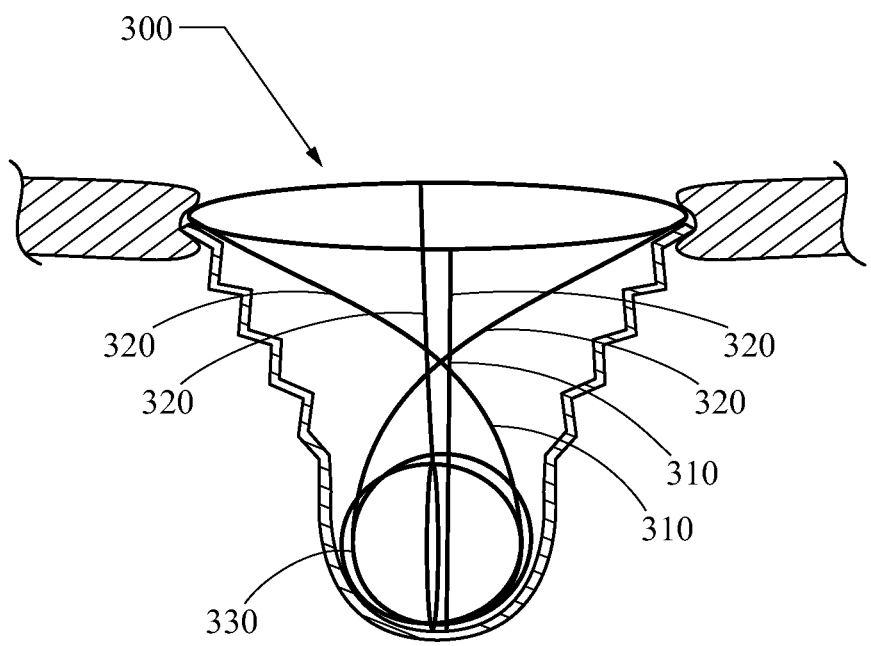

In certain instances, the device 300 may be supported by from 1 to 8 or more supporting wires. The device 300, may be supported by at least one supporting wire 310 as shown in FIG. 7A, which can be twisted to form 2 support elements 320 and at least 1 loop 330 to facilitate deployment and retrieval of the device. In certain instances, the device 300 may be supported by at least two supporting wires 310, which can be twisted to form 4 support elements 320 and at least 2 loops 330, as shown in FIG. 7B. In other instances (not shown), the device may include at least three supporting wires, which can be twisted to form 6 support elements and at least 3 loops. In yet other instances (not shown), the device may be supported by at least four supporting wires. In yet other instances (not shown), the device may be supported by at least five supporting wires. In some other instances, the device may be supported by at least six supporting wires. In yet further embodiments, the device may be supported by seven supporting wires. In other embodiments, the device may be supported by eight or more supporting wires.

In certain embodiments the filter could be supported by a mesh, cloth or netting made of suitable metals or nonmetals, including biological tissues, as described previously, that possesses larger open areas than in the filter, e.g., a net with 5 mm square openings holding a filter with 0.10 mm diameter pores.

Presence of the loops upon twisting of the wire configures the wire to have one end of the support elements to be circular and not sharp avoiding piercing though the filter and or filter material. The loops also may aid in withdrawal or retrieval of the device if the device ever needed to be retrieved from the blood vessel. For example, a physician may use a hook-like device to pull on the loops to retrieve the device from the body.

The support wires may be integral with the filter and or the frame or may be attached to the filter and or the frame by any suitable means, such as bonding, gluing, welding, etc. The support wires are provided with the device to add rigidity and structure to the device. The support wires also may aid during the movement of the device that results from the varying blood pressure (viz. diastolic and systolic) and blood flow, and especially when the support wires are formed from material such as nitinol. The support wires 350 also may form a filter support frame 360, as shown in FIG. 8. In certain embodiments, as shown, for example in FIG. 8, the filter is "inverted" into the common carotid artery. This type of filter may be self-cleaning, may be cleaned by aspiration of the surface of the filter, or alternatively, may be removed for cleaning.

Figure 9:
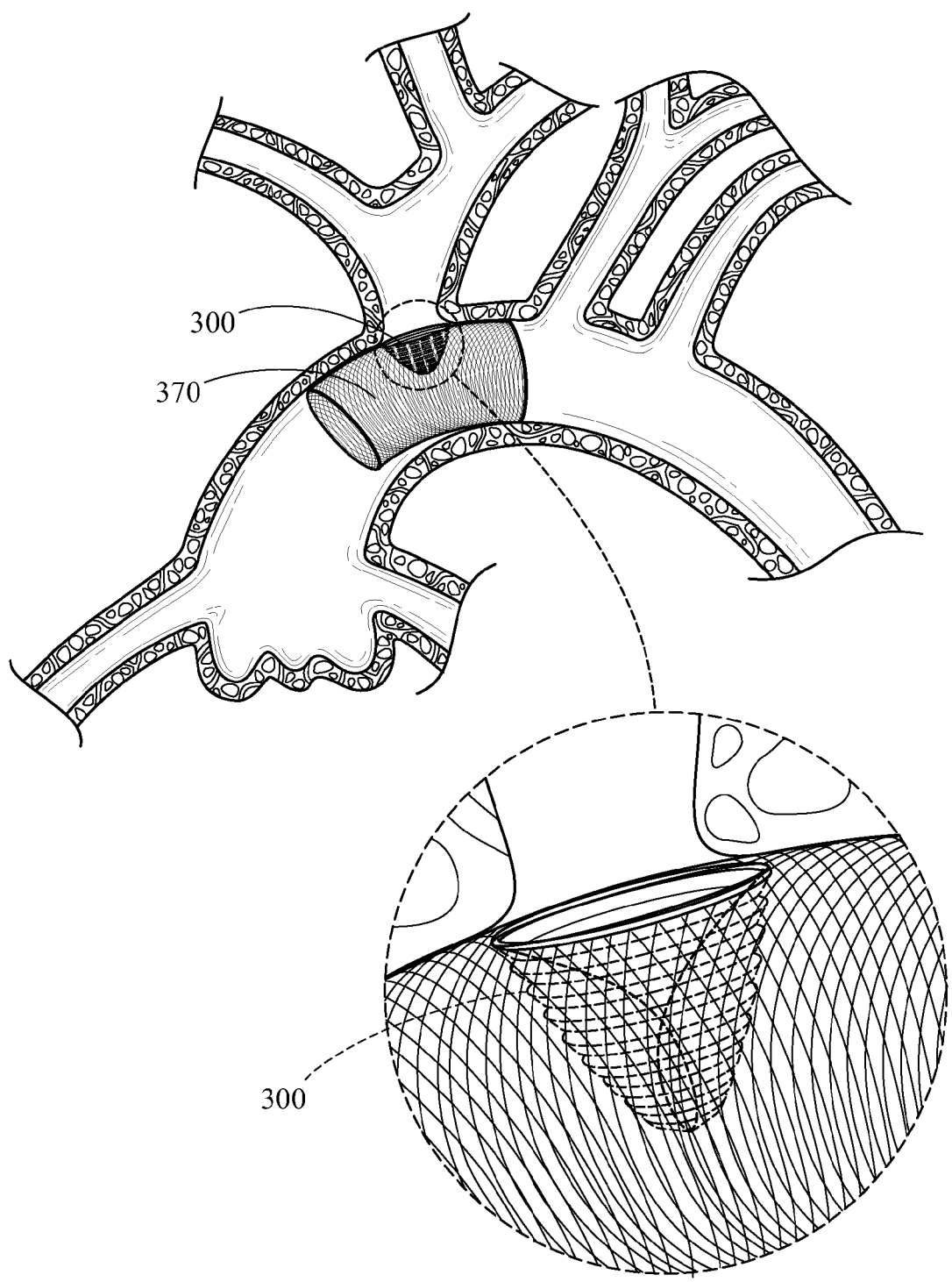
FIG. 9 is a schematic illustration of an exemplary device including a tubular member.

Referring to FIG. 9, the device 300 may be configured to attach to a tubular member 370. The tubular member 370 may be a stent-like tube or may be a stent 370. The tubular member in certain instances functions as a holder for the device. As illustrated in FIGS. 10A-10D, the stent may have any configuration adapted to maintain the lumen of a blood vessel at a desired degree of patency. The stent may be configured as a radially-expandable frame formed from a plurality of interconnected struts and bends forming a pair of longitudinally joined hoop members. Alternatively, a stent may include one or a plurality of radially-expanding stents such as Z-STENTS®, which are available from Cook, Incorporated (Bloomington, Ind.). The frame defines a tubular lumen and defines a plurality of openings between the lumen and the exterior surface of the frame.

The stent can be formed from any suitable biocompatible material providing properties suited for an intended application, such as desired rigidity or flexibility. The stent is capable of providing circumferential support while, at the same time, being axially flexible. The stent frame may be formed by forming the desired pattern directly out of a tube, e.g., by laser cutting or chemical etching. Alternatively, the desired pattern may be formed out of a flat sheet, e.g., by laser cutting or chemical etching, and then rolling that flat sheet into a tube and joining the edges, e.g., by welding. Any other suitable manufacturing method known in the art may be employed for manufacturing a stent. Furthermore, stents may be formed by etching a pattern into a material or mold and depositing stent material in the pattern, such as by chemical vapor deposition or the like. Such stents may be formed of plastic, metal or other materials and may exhibit a multitude of configurations. The metals from which such stents are formed may include stainless steels, titanium, Nitinol, and tantalum among others. The stent may be a stent graft and may include graft material such as DACRON, expanded polytetrafluoroethylene, or other suitable materials.

The stent may be moveable from a radially compressed state to the radially expanded state. In the radially compressed state, the stent may be symmetrically radially compressed about the longitudinal axis within the center of the tubular lumen and loaded into a suitable catheter-based endolumenal delivery system. The stent can be positioned at a point of treatment within a blood vessel using the delivery system and radially expanded by any suitable means to the radially expanded deployed state. Means for expanding the stent can include inflation of a balloon within the tubular lumen of the stent, or self-expansion of the stent upon removal of a means for radially constraining the stent in the radially compressed state. The frame may be configured and formed from materials that provide balloon-expandable or radially-expanding structures. Some exemplary stents are disclosed in U.S. Pat. Nos. 5,292,331; 6,090,127; 5,133,732; 4,739,762; and 5,421, 955.

Figure 10A:
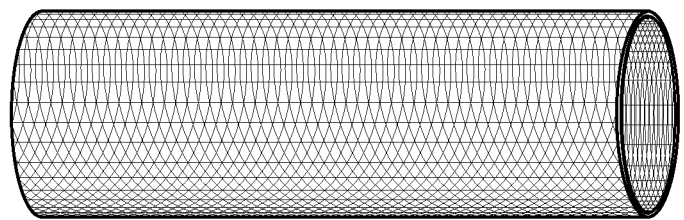
FIGS. 10A-10D are schematic illustrations of various exemplary stent configurations.
Figure 10B:
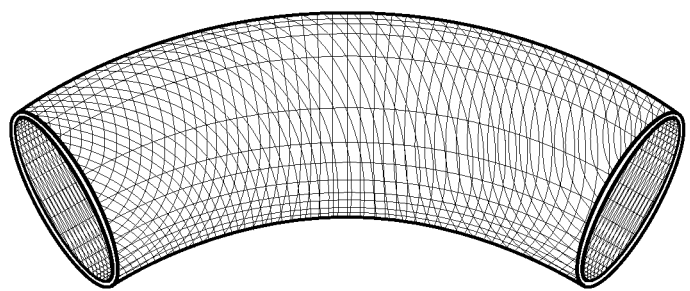
Figure 10C:
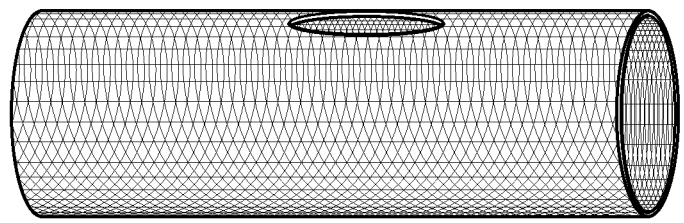

Exemplary stent configurations were also previously described in U.S. Pub. 2006/0161241 A1, which is incorporated by reference in its entirety. Specifically, the stent can be generally straight as depicted in FIG. 10A or curved as depicted in FIG. 10B. The stent may have one or more side openings as depicted in FIGS. 10C and 10D, respectively, to allow blood to flow into branching blood vessels.

Figure 10D:
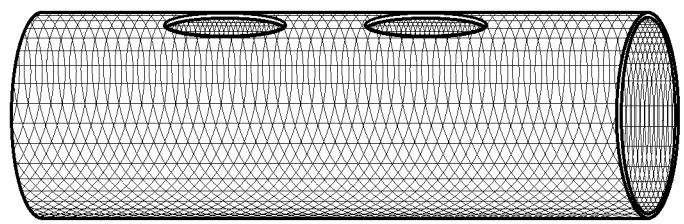
Figure 11A:
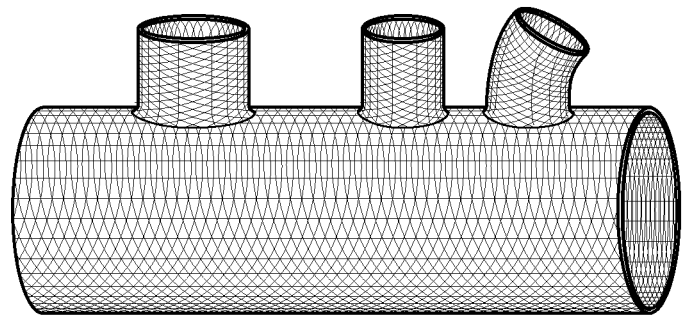
FIGS. 11A-11C are yet additional schematic illustrations of various exemplary stent configurations.
Figure 11B:
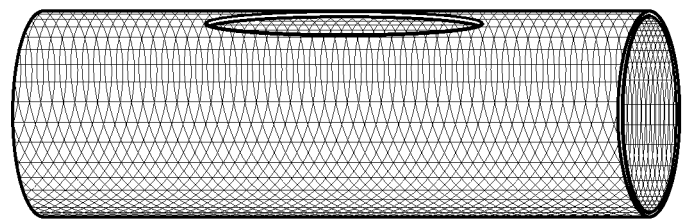
Figure 11C:
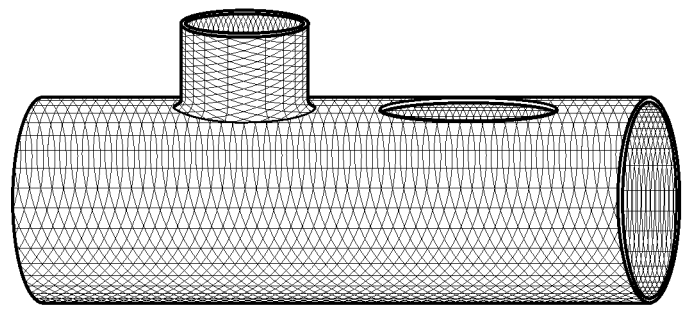

The stent may include at least one side opening, but may optionally include at least two or more side openings as depicted in FIG. 10D. The one or more side openings may, in certain cases, be equipped with sleeves that ensure proper alignment with vessels that branch from the aorta, as illustrated in FIGS. 11A and 11C. In other cases, as shown in FIG. 11B, the stent may include both an elongate side opening that allows blood flow to a number of vessels and a smaller opening, with or without sleeve.

The filter and or the frame of the device may be associated with the stent via either permanent or temporary association. For example, the frame may be bonded, soldered, sutured, glued or otherwise attached to the stent. In certain instances, the frame 180 is configured so that it can snap into the stent 370 to allow for later removal of the filtering device while leaving the stent in place, as shown in FIG. 7A and further in FIG. 12. Specifically, the opening in the stent may include a groove 380 or a clip into which the frame 180 may be inserted. The opening also may include hinges, hooks or other mechanism or shape into which the frame may be inserted, mounted, and secured.

As mentioned above, the filter may be removable and replaceable. Alternatively, the filter may configured for cleaning to allow removal from the filter of the filtrate that was not removed by the self-cleaning features of the device. One exemplary method of cleaning of the device includes providing a catheter, placing the catheter's opening against the filter element and aspirate the filtrate or embolic material away. Another exemplary method of cleaning the device includes applying an ultrasonic probe to the filter element to break the filtrate into smaller particles that then aspirating away or expelling the small pieces of filtrate by the self-cleaning feature.

The stents for use herein will generally range in length from 1 cm to 40 cm, in other cases from 1 cm to 20 cm, in other cases from 3 cm to 15 cm, and in other cases from 5 cm to 8 cm. The stents will typically have a diameter before expansion of 1-10 mm, in other instances 2-8 mm, and in other cases 3-7 mm. After expansion, the stent may reach a diameter of 3-4 cm, in other instances, 2-3 cm, and in other cases 1.5-2.5 cm depending on the location in the aorta and the anatomy of the individual patient. The forgoing ranges are intended only to illustrate typical device dimensions. Devices in accordance with the present invention can vary outside of these ranges without departing from the inventive principles taught herein.

Depending on the intended use of the device, the device may be deployed at a junction of first blood vessel and a second blood vessel and, optionally, a third blood vessel in the ascending aorta, the aortic arch, and or the descending aorta to trap and expel the embolic material from the device ultimately preventing embolic events in the brain, i.e., stroke. Other uses are also contemplated.

The device can be placed in a blood vessel using any known delivery device or system, which can include a catheter or a wire guide. Delivery systems having an outer diameter of from about 0.06 inches (5 French) to about 0.27 inches (20 French); preferably from about 0.10 inches (8 French) to about 0.22 inches (17 French); and most preferably from about 0.13 inches (10 French) to about 0.19 inches (14 French) may be used, although other sizes of the device delivery systems are also contemplated. The device may be placed in the blood vessel prior, with or after placing the tubular member in the blood vessel.

Figure 13A:
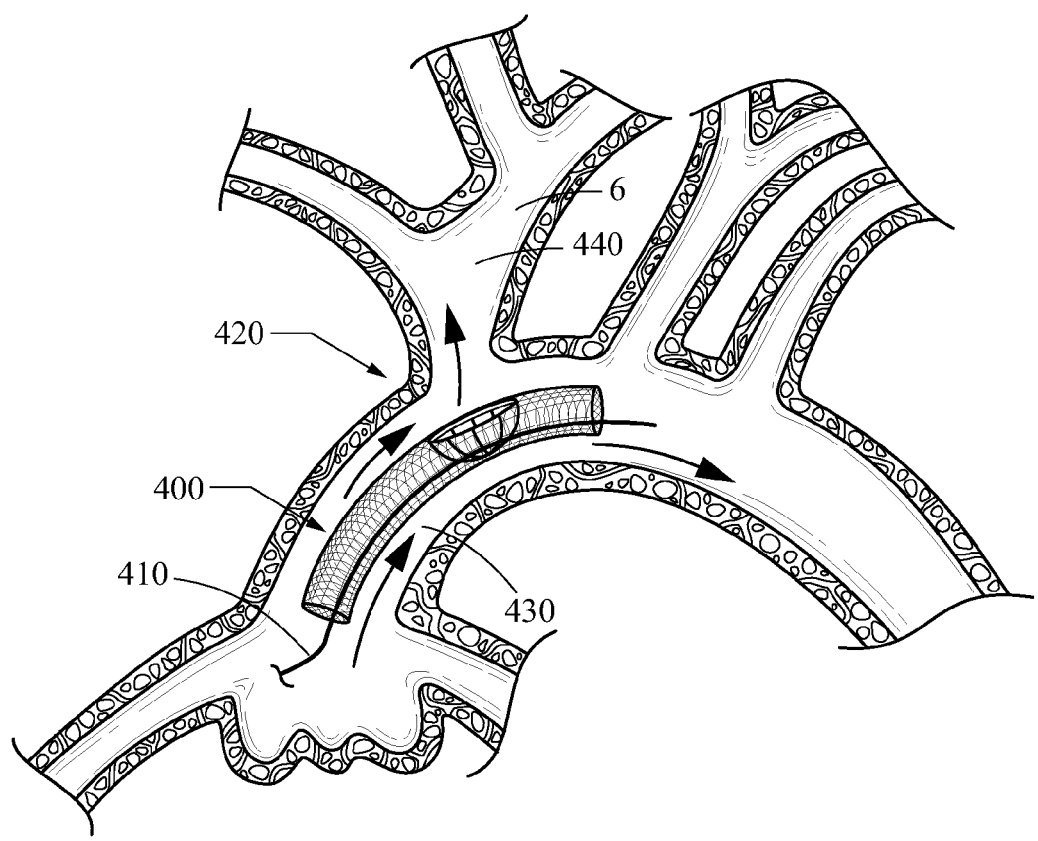
FIGS. 13A-13E illustrate a method of placing the device in the vasculature.
Figure 13B:
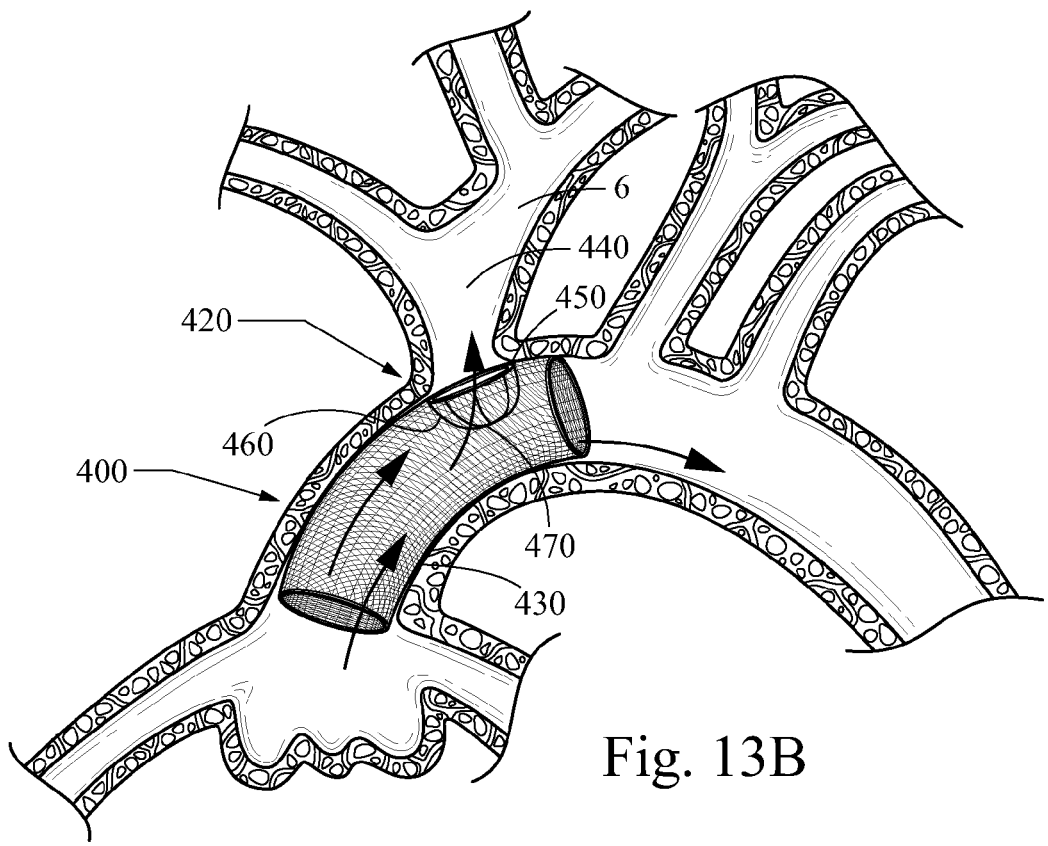

As illustrated in FIGS. 13A-B, the device 400 may be positioned on a wire guide 410, advanced through the vasculature of a patient and placed at or near a junction 420 of at least one branch blood vessel 440 and another blood vessel 430 so that a first end 450 of a flexible filter 460 resides at or near the junction 420, and a second end 470 of the flexible filter 460 extends at least partially within the other blood vessel 430. The direction of the blood flow though the vasculature is shown with arrows.

Figure 13C:
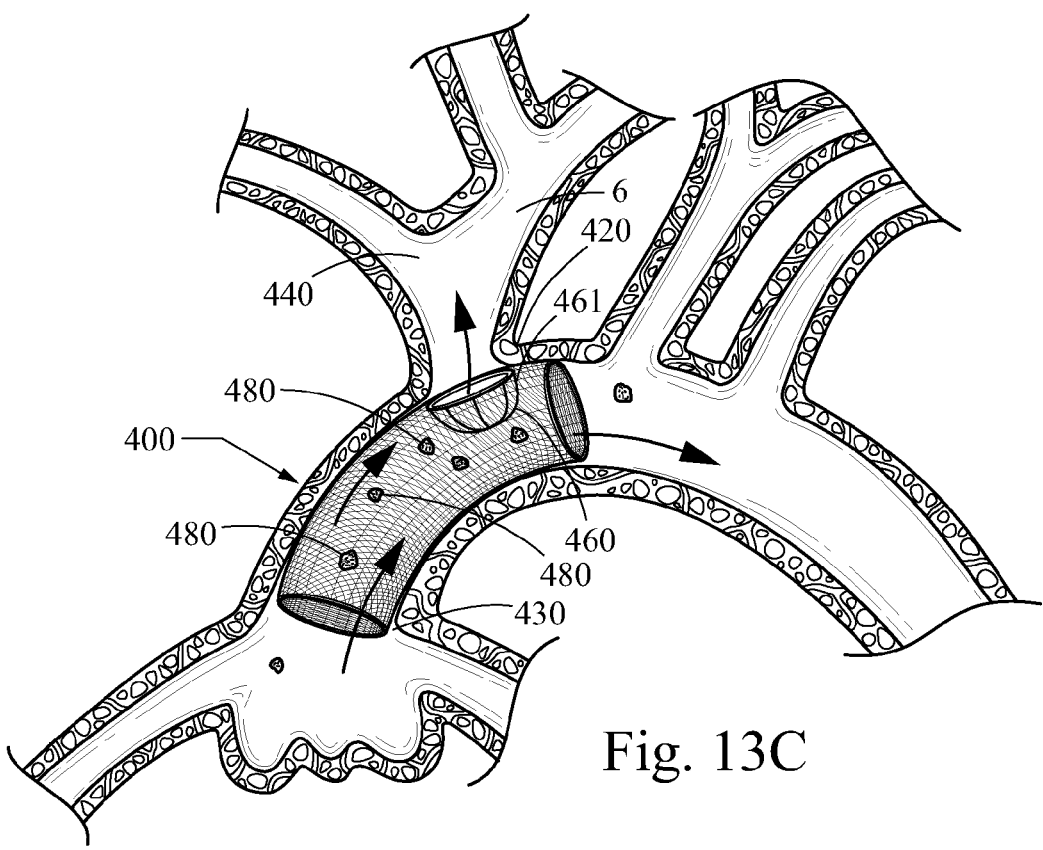
Figure 13D:
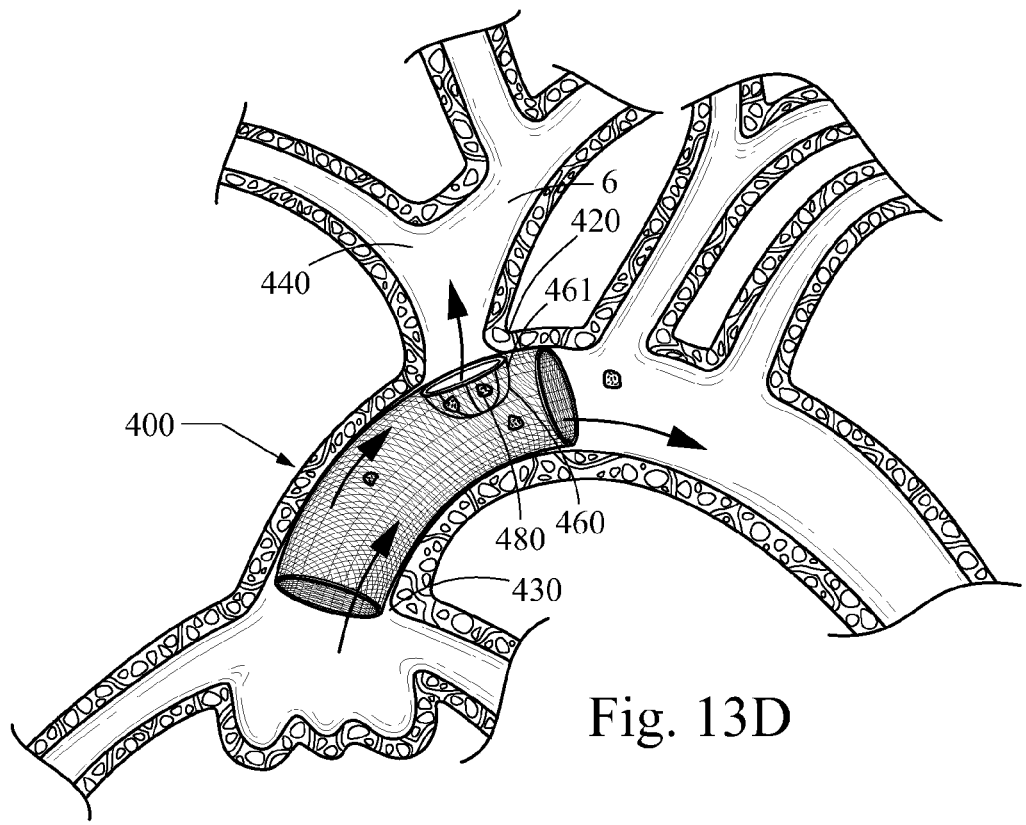

As further illustrated in FIGS. 13C-D, at least some of the embolic material 480 flowing about the junction 420 of the blood vessels 430, 440 becomes temporarily trapped on the external surface 461 of the flexible filter 460 (as shown in 13D) as a result of blood inflow (arrows) through and or across the surface of the filter. For clarity, the tubular member is shown without struts in these Figures.

Due to the inherent release force of the filter 460, the embolic material 480 that may become temporarily trapped on the external surface 461 of the filter 460 is then expelled from the filter back into the blood vessel 430 without entering the branch blood vessel 440.

In certain instances, referring still to FIGS. 13A-D, the junction is between the aorta 430 and the brachiocephalic artery 440. In those instances, the filter 460 is placed at or near the junction so that the inlet to the brachiocephalic artery 440 is covered with the filter 460. The embolic material that may temporarily become trapped on the external surface of the filter is expelled from the filter and, as such, prevented from entering the brachiocephalic artery 440 and as result also from entering the right common carotid artery 6.

Figure 13E:
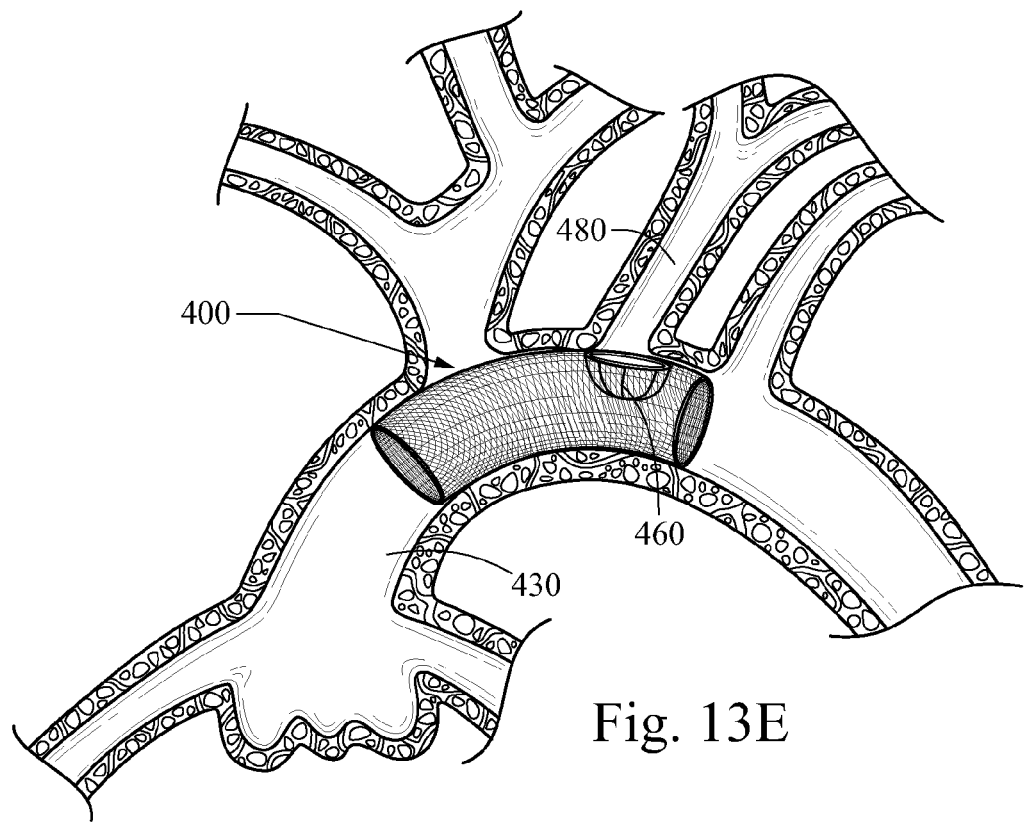

In certain other instances, referring to FIG. 13E, the junction is between the aorta 430 and the left common carotid artery 480. In those instances, the filter 460 is placed at or near the junction so that the inlet to the left common carotid artery 480 is covered with the filter 460. The embolic material that may temporarily become trapped on the external surface of the filter due to the blood inflow though the filter is then expelled from the filter back into the aorta and, as such, prevented from entering the left common carotid artery 480.

Figure 14:
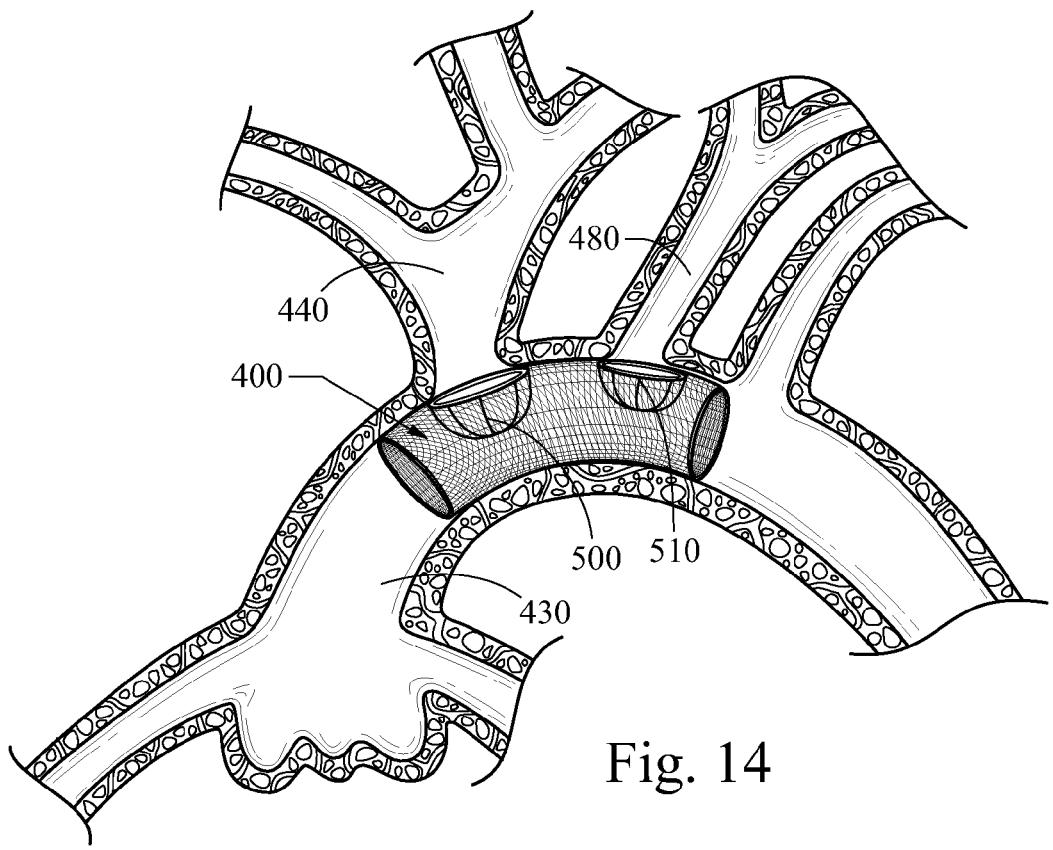
FIG. 14 depicts an exemplary device including two filters.
Figure 15:
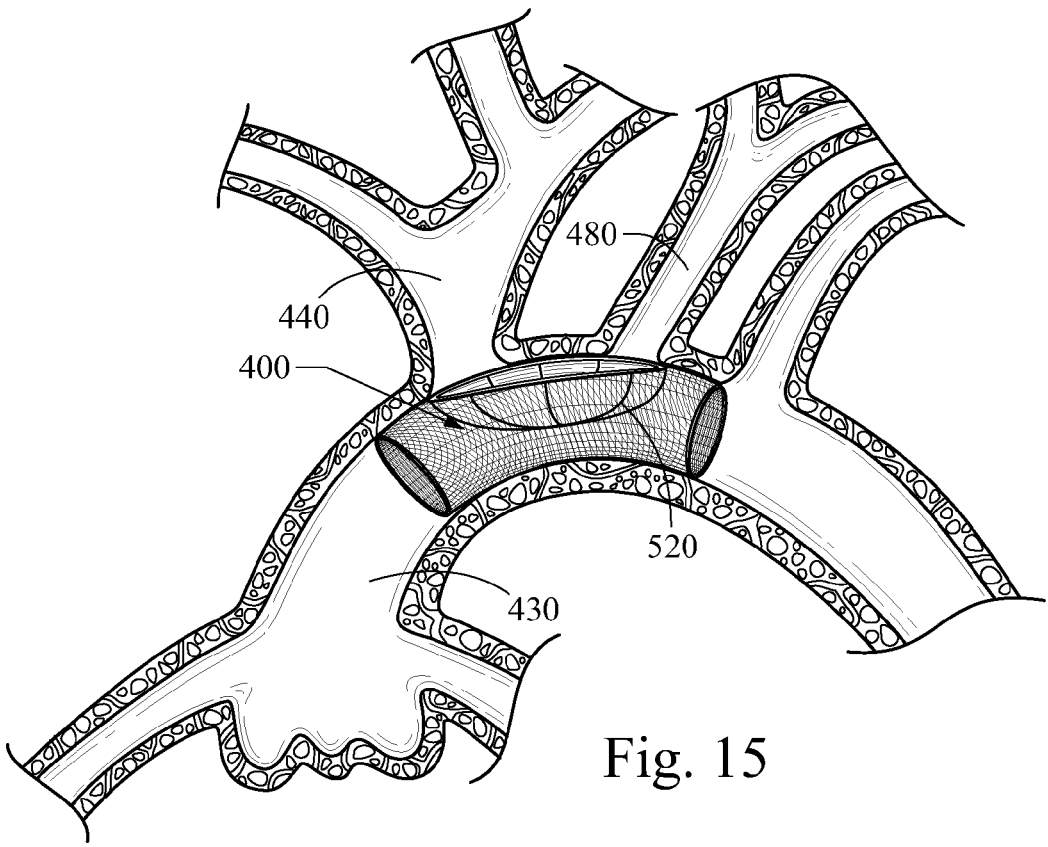
FIG. 15 depicts an exemplary device of this invention.

In certain other instances, as shown in FIGS. 14 and 15, the device may be used to prevent embolic material from entering both branch vessels (brachiocephalic artery 440 and left common carotid artery 480) by simultaneously covering the two branch vessels using a device including two separate filters 500, 510 (FIG. 14); or a device including one filter 520 that simultaneously covers the inlet to the brachiocephalic and the inlet to the left common carotid arteries (FIG. 15). In FIG. 14, the stent includes two separate openings, one for each filter.

Figure 16:
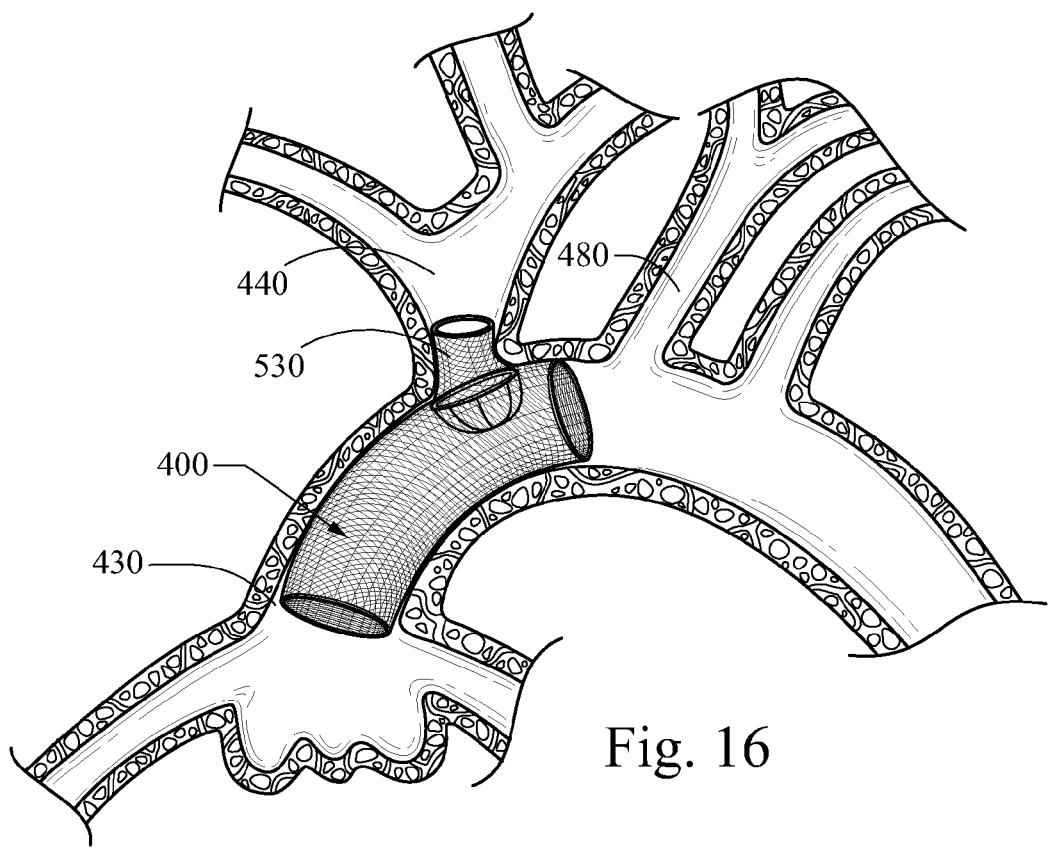
FIG. 16 depicts yet another example of a device of this invention.
Figure 17:
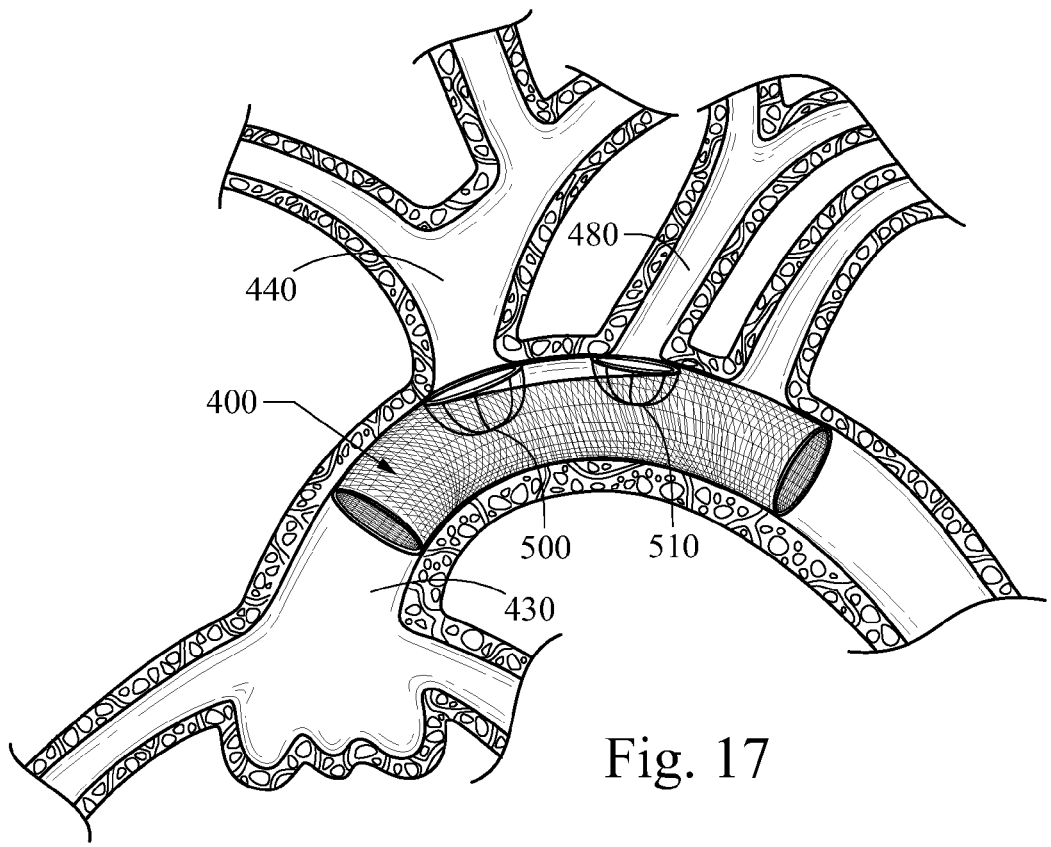
FIG. 17 depicts a further example of a device of this invention.

FIG. 16 illustrates an embodiment, where the device 400 includes a stent, the stent having a sleeve 530 that extends into the brachiocephalic artery 440. FIG. 17 illustrates yet another embodiment, where the device 400 includes two separate filters 550 and 510, one placed at a junction of aorta 430 and brachiocephalic artery 440 and second placed at a junction of aorta 430 and left common carotid artery 480. In this embodiment, the stent includes one opening for both filters 550 and 510.

FIGS. 18-21 illustrate some additional embodiments of the filter designs.

For example, in FIG. 18, a flat, pleated or corrugated cranial artery filter 800 is shown. The filter movement is illustrated with a straight arrow; cranial blood flow is illustrated with a curved arrow. The filter can include pleats 810, which can be linear or circular. A stent-like filter holder 820 may be used to hold the filter 800 in place at the junction of two blood vessels.

Figure 19:
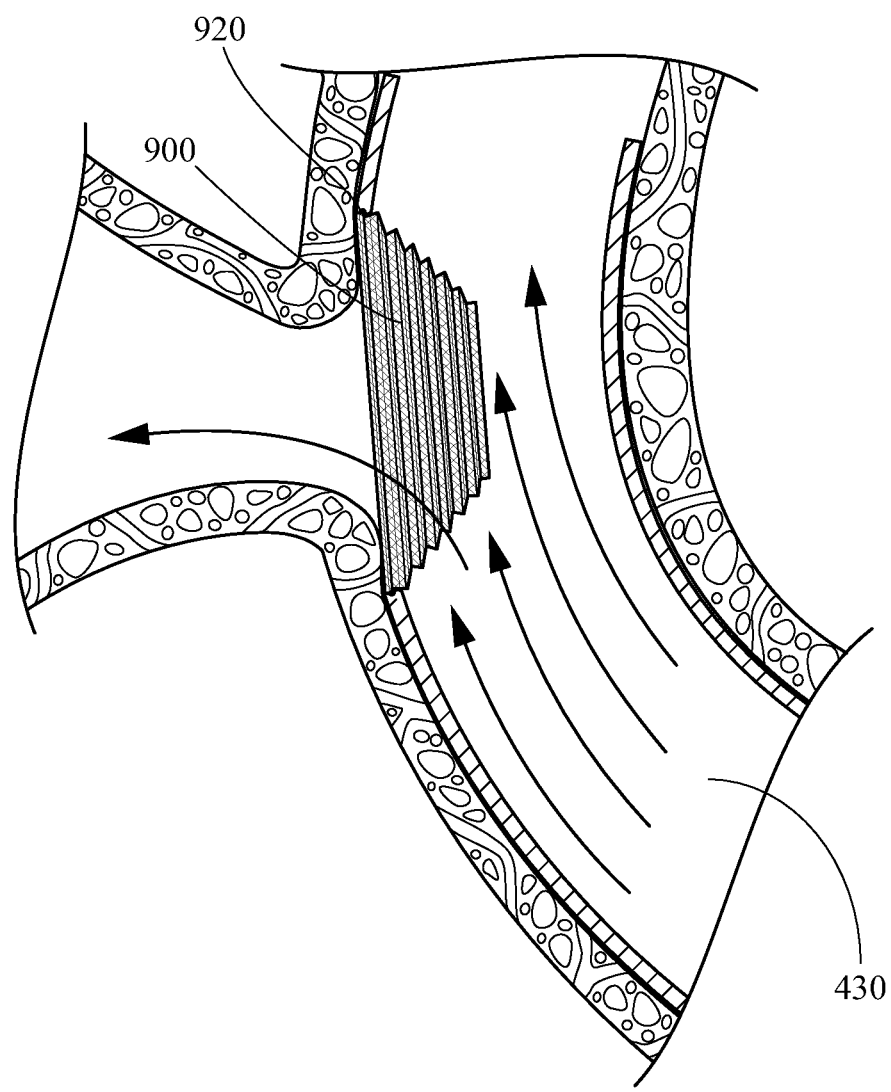
FIG. 19 depicts yet another example of a device of this invention having an enlarged hemisphere filter.

As illustrated in FIG. 19, an enlarged hemisphere filter 900 can be placed so that the filter element covers the carotid and brachiocephalic arteries simultaneously. The filter can include pleated rings 910. Blood flow is shown with curved arrows. A stent-like filter holder 920 may be used to hold the filter 900 in place at the junction of two blood vessels.

Figure 20:
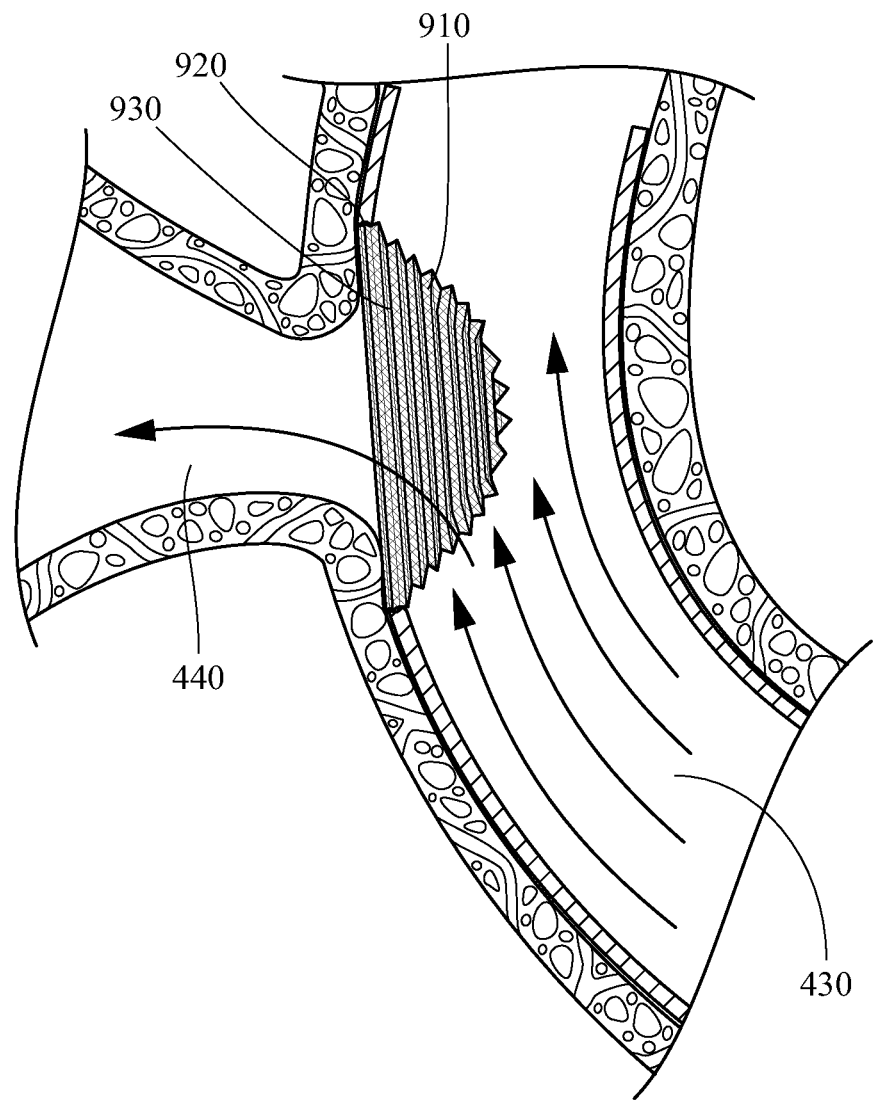
FIG. 20 depicts another example of a device of this invention having a hemisphere filter.

In another embodiment illustrated in FIG. 20, a hemisphere filter 930 that includes pleated rings 910 preferably made from elastomeric material can be placed at the junction of aorta 430 and left carotid artery or brachiocephalic artery 940. Blood flow is shown with curved arrows. A stent-like filter holder 920 may be used to hold the filter 930 in place at the junction of two blood vessels.

Figure 21:
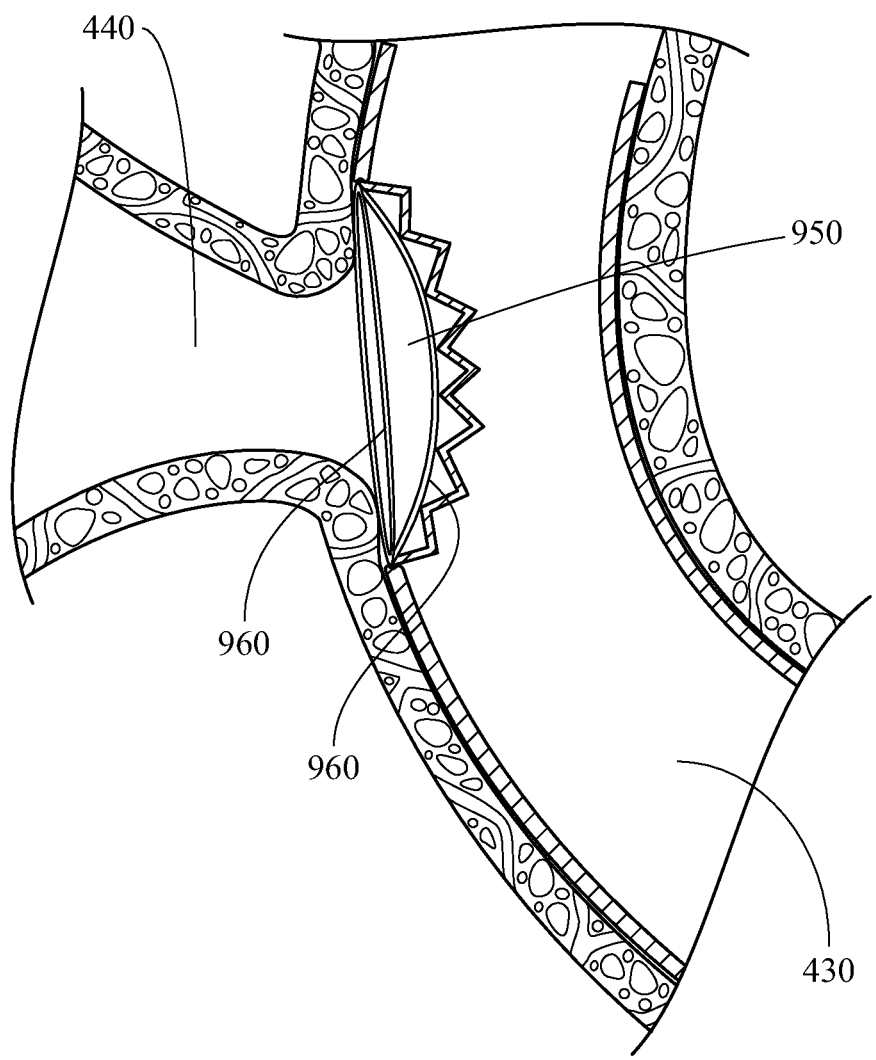
FIG. 21 depicts another example of a device of this invention.

In certain embodiments, as illustrated in FIG. 21, the filter element 950 can be prevented from bowing toward the lumen of the carotid artery 440 by support wires 960.

Any part of the device or the entire device may be selected and adapted to retain an effective amount of an agent that would enhance or induce endothelialization and or prevent or halt thrombogenesis and or prevent the growth of smooth muscle or other tissues on any part of the device. In certain embodiments, the platform (i.e. stent) and or the filter frame and or the filter elements are preferably nonthrombogenic. In certain embodiments, it may be desired to induce or enhance endothelialization of some or all surfaces of the device of this invention, and specifically, surfaces that contact the blood.

To do so, for example, the patient's own endothelial cells may be harvested and grown using tissue culture means prior to installation. Alternatively, some or all surfaces of the device may be patterned. Yet alternatively, the surfaces may be coated or sprayed with substances that are able to emit nitric oxide. Antibodies, such as anti-CD34, to circulating endothelial cells may be used to partially or completely coat the device of this invention. Other agents, such as AVI-4126 eluting phosphorylcholine (Kipshidze N N et al., *Catheter Cardiovac Interv.*, 61(4):518-527 (2004)), AVI-5126 or Resten-NG (AVI, Inc.) also may be used. In certain further embodiments, at least a portion of the device may be coated with peptides derived from fibronectin type II, which inhibit platelet adhesion and as such prevent thrombogenesis (Rodenberg E J and Pavalko F M, *Tissue Engineering*, 13(11): 2653-2666 (2007)). Yet alternatively, AVI-5126 antisense agent may be delivered to the site of installation of the device and filter prior to the installation. Other method and agents that may prevent device thrombogenesis may be used with the device of this invention.

The agent(s) that would enhance or induce endothelialization and or prevent or halt thrombogenesis may be for example, admixed with excipients or carriers suitable for either enteral or parenteral application. In certain instances, the agents may be admixed with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; and/or if desired c) disintegrants, e.g., starches, agar, alginic acid or its sodium salt, or effervescent mixtures. These compositions may be sterilized and/or contain adjuvants, such as preserving, stabilizing, wetting or emulsifying agents, solution promoters, salts for regulating the osmotic pressure and/or buffers. In addition, they also may contain other therapeutically valuable substances. These compositions may be prepared according to conventional mixing, granulating or coating methods, respectively. These compositions may contain about 0.1 to 95% of the desired agent. In certain instances, the compositions may contain about 0.1 to 75% of the desired agent. In yet other instances, the compositions may contain about 1 to 50% of the desired agent.

The agents and or compositions may, for example, be included as part of at least a portion of the material of the medical device itself; be contained within a reservoir, a well or a groove; be within a carrier material deposited on at least a portion of the medical device, or as a separate layer deposited on at least a portion of the medical device (the layer may optionally be over coated with another layer) or on at least a portion of the medical device that has been coated with a primer layer for increased adhesion; or within the hollow walls of the device; or any combination of these. These active agents and or compositions may be coated, sprayed, impregnated and otherwise incorporated into at least portions of the medical device. For example, the filtering element may be impregnated with the pharmaceutically active agents. Various methods of incorporating or coating medical devices with desired pharmaceutical or biological agents are known in the art and will not be described herein in more detail for the sake of brevity.

For placing the device described herein, conventional stent deployment equipment may be used, which equipment typically includes an expandable balloon, fitted on an end of an inflating tube carried by a guide wire. However, the device also may be self expandable, as known per se and as readily understood by the skilled person.

In certain instances, the device or any part thereof discussed herein may need to be removed for cleaning or may need to be replaced. To remove the filter, a physician can use a catheter with a distal end configured to hold the filter in a specified position during insertion into the aortic arch. The catheter can then effect the filter element release while retaining it for further positioning. In certain embodiments, a second catheter, the distal end of which bears specialized grasping mechanisms for further positioning the filter element into its supporting structure, may be used. Methods of removal of stent-like tubular elements are known in the art.

The devices, systems and procedures described herein have various applications. Some illustrative applications include: embolic strokes from proximal sources (e.g., mechanical heart valves, Afib, LVT, protruding aortic arch atheroma (AAA)), which include: atrial fibrillation, mechanical heart valves, patients at high risk for recurrent embolism for a certain period, patients at high risk for proximal emboli and absolute contraindications for anticoagulation, and patients at high risk for proximal emboli failing best medical treatment; severe carotid stenosis with concomitant high risk (protruding AAA; severe carotid stenosis with concomitant cardiac disease; severe carotid stenosis in patients who underwent heart surgery); and others.

The invention also relates to a method of preventing embolic material flowing about a junction of at least one branch blood vessel and another blood vessel from entering the at least one branch blood vessel. The method includes placing at the junction a device comprising a self cleaning flexible filter, the flexible filter having a first end, a second end, an external surface, and a filter release force, the first end configured to reside at or near the junction, and the second end configured to extend at least partially within the other blood vessel, and a frame positioned at least at the first end of the filter and configured to hold the first end of the filter at the junction. The method also includes temporarily trapping on the external surface of the filter at least some of the embolic material flowing about the junction as a result of blood inflow though the filter and via a release force expelling the embolic material from the filter into the other blood vessel. Also, a tubular member may be placed at or near the junction together with, prior to or after placement of the filter and the frame. This method may be for prevention of embolic stroke in a subject.

While various embodiments of the invention have been described, it will be apparent to those of ordinary skill in the art that many more embodiments and implementations are possible within the scope of the invention. Accordingly, the invention is not to be restricted except in light of the attached claims and their equivalents.

I claim:

1. A self cleaning device, comprising:
   a first flexible filter comprising tapered pores and having a first end, a second end, and a first external surface, the first end configured to reside at or near a junction of at least one branch blood vessel and another blood vessel, and the second end configured to extend at least partially within the other blood vessel; and
   a first frame positioned at least at the first end of the first filter and configured to hold the first end of the first filter at the junction of the at least one branch blood vessel and the other blood vessel;
   where the first external surface of the first filter has a first configuration adapted to temporarily trap at least some of the embolic material flowing about the junction of the at least one branch blood vessel and the other blood vessel as a result of blood inflow through the first filter, and a second configuration adapted to expel the trapped embolic material into the other blood vessel.

2. The device of claim 1, wherein the pores range in size from about 0.02 mm to about 0.5 mm.

3. The device of claim 2, wherein the pores form a taper or a cylindrical hole as a result of the first flexible filter release force.

4. The device of claim 2, wherein the first filter comprises a material selected from the group consisting of polytetrafluoroethylene, polyurethane, and silicone rubbers.

5. The device of claim 1, wherein the first filter comprises pleats.

6. The device of claim 1, further comprising at least one supporting wire, the supporting wire comprising two support elements and at least one loop.

7. The device of claim 6, wherein the support elements comprise nitinol.

8. The device of claim 1, wherein the first filter, the first frame, or both comprise at least one agent to enhance endothelialization or to prevent the growth of smooth muscle or certain other tissues on any surface of the first filter, the first frame, or both.

9. The device of claim 8, wherein the agent is selected from the group consisting of endothelial cells derived from the subject prior to installation of the device in the subject, a nitric oxide emitter compound, an antibody to circulating progenitor cells, at least one fibronectin-derived low-molecular-weight peptide fragment, Resten-NG, AVI-4126, and AVI-5126.

10. The device of claim 1, wherein the at least one branch blood vessel is the brachiocephalic artery and the other blood vessel is the aorta.

11. The device of claim 1, further comprising a tubular member configured to hold at least the first filter.

12. The device of claim 11, wherein the tubular member is a stent.

13. The device of claim 1, wherein the first flexible filter has an open area of at least 50%.

14. The device of claim 1, wherein the first flexible filter is configured to be replaced.

15. The device of claim 1, wherein the device is configured for permanent implantation into a subject.

16. The device of claim 1, further comprising
   a second flexible filter, the second filter having a first end, a second end, a second external surface, and a second release force, the first end of the second filter configured to reside at or near a junction of the at least one branch blood vessel and the other blood vessel, and the second end of the second filter configured to extend at least partially within the other blood vessel; and
   a second frame positioned at least at the first end of the second filter and configured to hold the first end of the second filter at the junction of the at least one branch blood vessel and the other blood vessel;
   wherein the second external surface of the second filter is configured to temporarily trap at least some of the embolic material flowing about the junction of the at least one branch blood vessel and the other blood vessel as a result of blood inflow though the second filter, and wherein the second external surface of the filter is further configured to expel the trapped embolic material into the other blood vessel as a result of a second filter release force.

17. The device of claim 16, wherein the at least one branch blood vessel includes the brachiocephalic artery and left common carotid artery, and the other blood vessel is the aorta.

18. The device of claim 16, further comprising a tubular member configured to hold at least the first filter and the second filter.

19. A method for preventing embolic stroke in a subject, the method comprising placing the device of claim 1 at the junction of the at least one branch blood vessel and the other blood vessel.

20. A method for preventing embolic stroke in a subject, the method comprising placing the device of claim 16 at the junction of the at least one branch blood vessel and the other blood vessel.

\* \* \* \* \*